United States Patent
Ikemoto et al.

(10) Patent No.: US 9,398,127 B2
(45) Date of Patent: Jul. 19, 2016

(54) PORTABLE TERMINAL AND SKIN PROPERTY MEASURING INSTRUMENT

(71) Applicant: Panasonic Intellectual Property Management Co., Ltd., Osaka (JP)

(72) Inventors: Koichi Ikemoto, Hyogo (JP); Hirokazu Kitamura, Osaka (JP); Yasuhiro Hibino, Osaka (JP); Takahiro Miyatake, Osaka (JP); Yoshiyuki Kajimoto, Osaka (JP); Fumiyasu Konno, Osaka (JP); Katsu Takeda, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/406,237

(22) PCT Filed: Jun. 24, 2013

(86) PCT No.: PCT/JP2013/003916
§ 371 (c)(1),
(2) Date: Dec. 8, 2014

(87) PCT Pub. No.: WO2014/006839
PCT Pub. Date: Jan. 9, 2014

(65) Prior Publication Data
US 2015/0156298 A1 Jun. 4, 2015

(30) Foreign Application Priority Data

Jul. 5, 2012 (JP) .................................. 2012-151090
Jul. 6, 2012 (JP) .................................. 2012-152465
Jul. 6, 2012 (JP) .................................. 2012-152470

(51) Int. Cl.
*H04M 1/00* (2006.01)
*H04M 1/21* (2006.01)
(Continued)

(52) U.S. Cl.
CPC ............... *H04M 1/21* (2013.01); *A61B 5/0531* (2013.01); *A61B 5/0537* (2013.01); *A61B 5/443* (2013.01); *A61B 5/6898* (2013.01); *H04M 1/72522* (2013.01); *A61B 2560/0462* (2013.01); *A61B 2560/0468* (2013.01); *H04M 2250/52* (2013.01)

(58) Field of Classification Search
CPC ...... A61B 5/01; A61B 5/422; A61B 5/14532; A61B 5/0002; A61B 5/0059; H04M 1/72522
USPC ............... 455/556.1; 600/301, 306, 340, 407; 345/157
See application file for complete search history.

(56) References Cited

U.S. PATENT DOCUMENTS

| | | | |
|---|---|---|---|
| 6,871,242 B1 * | 3/2005 | Ho-Lung | G06K 9/00107 345/157 |
| 2002/0115926 A1 * | 8/2002 | Takada | A61B 5/0059 600/407 |

(Continued)

FOREIGN PATENT DOCUMENTS

| | | |
|---|---|---|
| DE | 10 2010 019 104 A1 | 11/2011 |
| EP | 2 638 929 A1 | 9/2013 |

(Continued)

OTHER PUBLICATIONS

Extended European Search Report issued Jun. 24, 2015, in related European Patent Application No. 13813847.4.

(Continued)

*Primary Examiner* — William D Cumming
(74) *Attorney, Agent, or Firm* — Wenderoth, Lind and Ponack, L.L.P.

(57) ABSTRACT

A portable terminal includes a case, a display unit having a display screen exposed from a front surface of the case, and a skin-condition measurement sensor accommodated in the case. The skin-condition measurement sensor includes a measurement unit provided on the front surface of the case. The portable terminal can be carried and operate easily.

14 Claims, 23 Drawing Sheets

(51) Int. Cl.
*A61B 5/00* (2006.01)
*A61B 5/053* (2006.01)
*H04M 1/725* (2006.01)

(56) References Cited

U.S. PATENT DOCUMENTS

| | | | |
|---|---|---|---|
| 2004/0225207 A1* | 11/2004 | Bae | A61B 5/0002 |
| | | | 600/340 |
| 2007/0276206 A1* | 11/2007 | Takeuchi | A61B 5/442 |
| | | | 600/306 |
| 2008/0137896 A1 | 6/2008 | Tsen | |
| 2009/0287067 A1 | 11/2009 | Dorogusker et al. | |
| 2012/0116184 A1* | 5/2012 | Shieh | A61B 5/01 |
| | | | 600/301 |
| 2012/0123222 A1* | 5/2012 | Chen | A61B 5/14532 |
| | | | 600/301 |
| 2012/0156933 A1 | 6/2012 | Kreger et al. | |
| 2012/0231841 A1 | 9/2012 | Niederberger et al. | |
| 2013/0218067 A1 | 8/2013 | Saito et al. | |

FOREIGN PATENT DOCUMENTS

| | | |
|---|---|---|
| JP | 3074054 | 12/2000 |
| JP | 2003-018250 | 1/2003 |
| JP | 2003-319910 | 11/2003 |
| JP | 2004-193703 | 7/2004 |
| JP | 2004-274404 | 9/2004 |
| JP | 2005-054809 | 3/2005 |
| JP | 2006-349625 | 12/2006 |
| JP | 2008-167205 | 7/2008 |
| JP | 2008-205591 | 9/2008 |
| JP | 2009-065390 | 3/2009 |
| JP | 2010-284239 | 12/2010 |
| JP | 3173514 | 2/2012 |
| JP | 2012-191619 | 10/2012 |
| WO | 2012/063883 | 5/2012 |

OTHER PUBLICATIONS

International Search Report issued Aug. 27, 2013 in International (PCT) Application No. PCT/JP2013/003916.

* cited by examiner

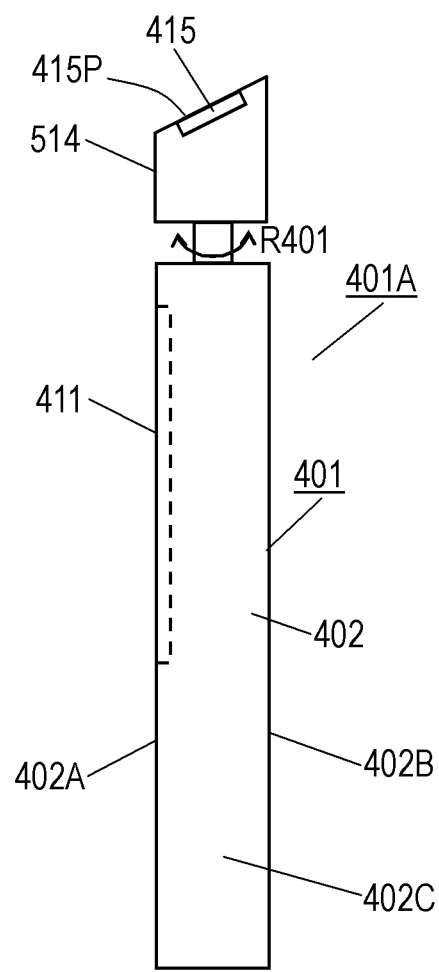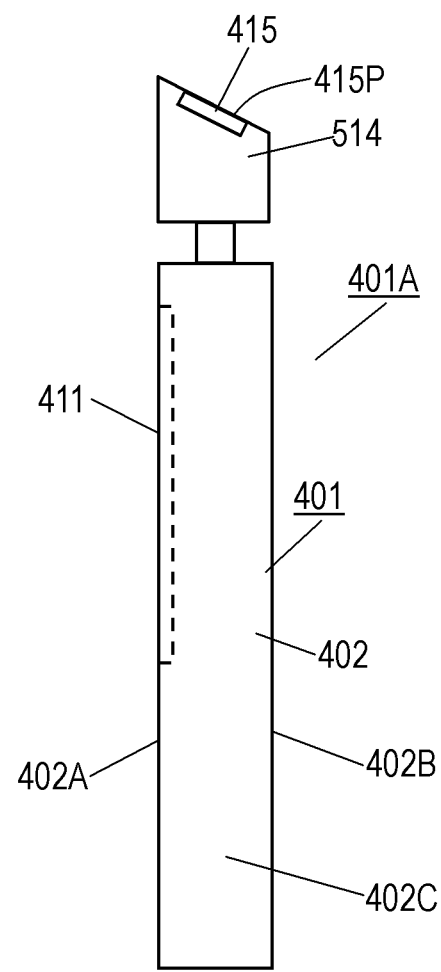

PORTABLE TERMINAL AND SKIN PROPERTY MEASURING INSTRUMENT

This application is a U.S. national stage application of the PCT international application No. PCT/JP2013/003916, filed Jun. 24, 2013.

TECHNICAL FIELD

The present invention relates to a portable terminal, such as a portable phone, a personal handy-phone system (PHS), a personal digital assistant (PDA), a personal computer, a portable tool, an electronic dictionary, an electronic calculator, or a game device, capable of measuring a skin condition, and to a skin-condition measurement device.

BACKGROUND ART

PTL 1 discloses a portable measurement device having a sensor for measuring moisture and sebum of the skin, and a data communication portable terminal connected to the portable measurement device. The portable measurement device and the data communication portable terminal are separate devices. A skin condition is measured remotely from the data communication portable terminal.

PTL 2 discloses a portable phone receiving user's skin moisture information.

CITATION LIST

Patent Literatures

PTL 1: Japanese Patent Laid-Open Publication No. 2003-319910

PTL 2: Japanese Patent Laid-Open Publication No. 2003-18250

SUMMARY

A portable terminal includes a case, a display unit having a display screen exposed from a front surface of the case, and a skin-condition measurement sensor accommodated in the case. The skin-condition measurement sensor includes a measurement unit provided on the front surface of the case.

The portable terminal can be carried and operate easily.

BRIEF DESCRIPTION OF DRAWINGS

FIG. 27A is a side view of a portable terminal according to Exemplary Embodiment 9 of the present invention.

FIG. 27B is a side view of the portable terminal according to Embodiment 9.

DETAILED DESCRIPTION OF PREFERRED EMBODIMENTS

Exemplary Embodiment 1

Figure 1:
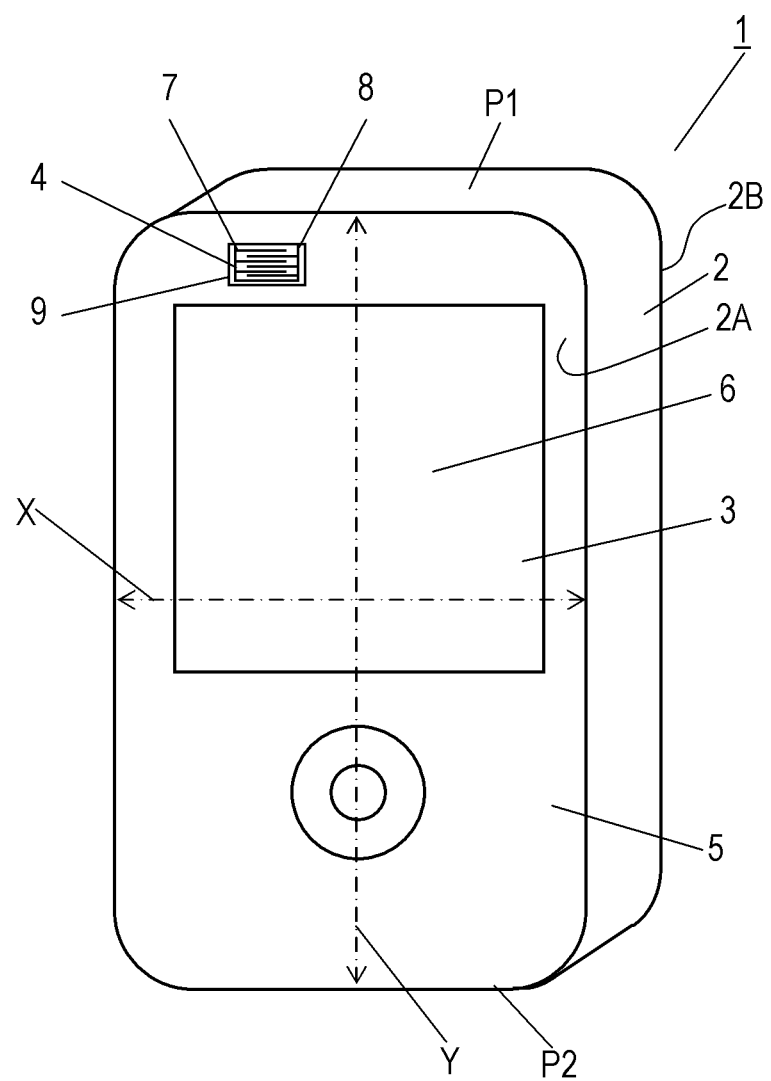
FIG. 1 is a perspective view of a portable terminal according to Exemplary Embodiment 1 of the present invention.

FIG. 1 is a perspective view of portable terminal 1 according to Exemplary Embodiment 1 of the present invention.

Portable terminal 1 according to Embodiment 1 is a high-functionality portable phone called a smart phone.

Portable terminal 1 can be used not only for mutual data communications, such as phone communications or sending/receiving of email, but also for playing or storing media or browsing websites. Portable terminal 1 may be operable with both wireless and wired communications.

As shown in FIG. 1, portable terminal 1 includes case 2, display unit 3, and skin-condition measurement sensor 4 accommodated in case 2. Case 2 has an opening and front plate 5 covering the opening. Case 2 has front surface 2A that is the surface of front plate 5, and rear surface 2B opposite to front surface 2A.

Case 2 covers a front surface, a rear surface, and side surfaces of portable terminal 1. Case 2 has a cavity provided therein. Display unit 3 and skin-condition measurement sensor 4 are accommodated in this cavity.

Case 2 further accommodates, in the cavity, integrated circuits and other circuits that execute operations of portable terminal 1. The Integrated circuits and other circuits include microprocessors, memories, a battery for driving portable terminal 1, circuit boards, input/output circuits, and various input/output assistance circuits. Portable terminal 1 further includes an antenna. The antenna may be exposed outside case 2, or accommodated in case 2. The wireless communications may be based on various communication protocols, such as high frequency communications, Bluetooth™.

Display unit 3 includes, for example, a touchscreen and display screen 6 implemented by a liquid crystal display, such as an organic liquid crystal display.

Front plate 5 covering the opening of case 2 has a transparent plate portion made of glass or acrylic at least above display screen 6. Display screen 6 faces outside of portable terminal 1 via front plate 5, i.e., front surface 2A of case 2. In other words, a user can see display screen 6 through transparent front plate 5.

A cross section of case 2 parallel to display screen 6 has substantially a rectangular shape which has long axis Y and short axis X and which is elongate along long axis Y. According to Embodiment 1, case 2 may have an oval cross-sectional shape. Case 2 may have various other shapes, such as a square or circle shape. Rectangular or oval shapes that have long axis Y and short axis X and are elongate along long axis Y can be held easily by the user since the shapes allow to case 2 to be used in a vertical orientation along the direction of long axis Y, and to be used easily since the shapes are long enough to extend from an ear to the mouth of the user.

Skin-condition measurement sensor 4 includes measurement unit 9 that measures a skin condition of the user and a circuit module that processes signals from measurement unit 9. According to Embodiment 1, skin-condition measurement sensor 4 of portable terminal 1 is a moisture sensor that measures moisture content of a skin of the user. Other than moisture, skin-condition measurement sensor 4 may measure various other skin conditions, such as temperature, sebum content, color, or brightness.

The moisture sensor according to Embodiment 1 determines the moisture content of the skin based on a capacitance. A pair of electrodes contact or approach a skin surface changes the dielectric constant between the electrodes. The change in the capacitance is detected based on this change in the dielectric constant to calculate the moisture content of the skin. With the use of comb electrodes 7 and 8, a large value of capacitance can be detected, so that a higher degree of measurement accuracy is achieved. Parameters, such as a resistance or impedance, other than the capacitance between the electrodes may be used to determine the moisture content of the skin.

Brightness, color, and temperature of the skin may be measured with, e.g. an infrared sensor as skin-condition measurement sensor 4. A sebum content of the skin may be measured with, e.g., an optical sensor as skin-condition measurement sensor 4. The optical sensor emits light to a sampling surface and measures the intensity of light reflected from the surface.

Figure 2:
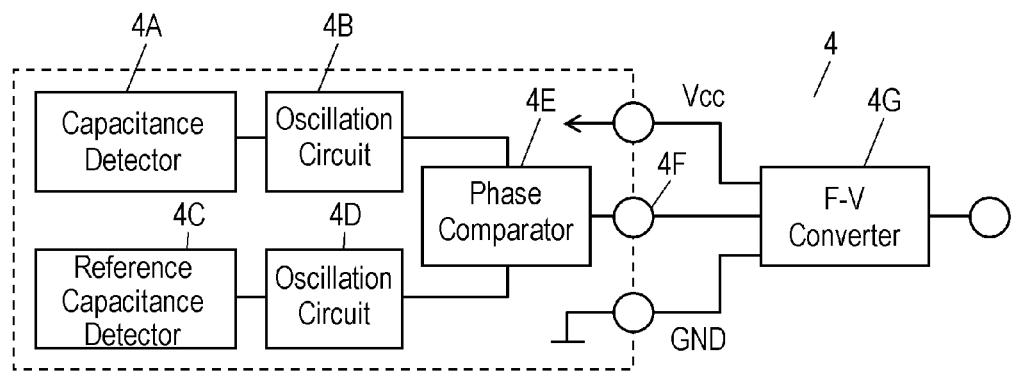
FIG. 2 is a block diagram of a skin-condition measurement sensor of the portable terminal according to Embodiment 1.

FIG. 2 is a block diagram of a capacitive moisture sensor constituting skin-condition measurement sensor 4.

Skin-condition measurement sensor 4 includes capacitance detector 4A that detects a capacitance between electrodes that corresponds to the moisture content of the skin, and oscillation circuit 4B connected to an output port of capacitance detector 4A to detect the capacitance based on a frequency. Capacitance detector 4A corresponds to measurement unit 9 shown in FIG. 1.

Skin-condition measurement sensor 4 further includes reference capacitance detector 4C that detects the capacitance between electrodes changing in accordance with ambient conditions, such as a temperature or humidity, and oscillation circuit 4D connected to an output port of reference capacitance detector 4C to detect the capacitance based on a frequency.

Phase comparator 4E is connected to output ports of oscillation circuits 4B and 4D. Phase comparator 4E detects a difference of the frequencies of oscillation circuits 4B and 4D. Output terminal 4F is connected to an output port of phase comparator 4E. Output terminal 4F is connected to frequency-voltage (F-V) converter 4G.

F-V converter 4G converts a signal representing the difference of the frequencies into an analog voltage. The Voltage output from F-V converter 4G can be converted to the moisture content of the skin by a predetermined algorithm since the voltage corresponds to the moisture content. A calculation result of the moisture content of the skin may be displayed on display unit 3 so that the user can realize the moisture content of the skin.

While portable terminal 1 according to Embodiment 1 measures humidity and temperature with reference capacitance detector 4C separately from capacitance detector 4A (measurement unit 9) for measuring the moisture content of the skin so as to eliminate an influence of the ambient conditions, portable terminal 1 according to Embodiment 1 can measure the moisture content only with capacitance detector 4A without using reference capacitance detector 4C. In this case, a reference capacitance of a surrounding ambient condition may be detected as an initial value, and then, a difference from a capacitance corresponding to the moisture content of the skin may be determined. If the ambient conditions have little influence on the measurement, skin-condition measurement sensor 4 may not necessarily include reference capacitance detector 4C, oscillation circuit 4D, and phase comparator 4E.

The capacitive moisture sensor is not limited to the sensor shown in FIG. 2 and may have various configurations. For example, instead of detecting the capacitance with oscillation circuit 4B shown in FIG. 2, the capacitance may be detected based on a difference in amplitudes. In this case, a lock-in amplifier may be used instead of oscillation circuit 4B, for example. While portable terminal 1 according to Embodiment 1 includes F-V converter 4G to convert a signal representing the difference in the frequencies to the analog voltage, the signal may be converted to a bus signal, using, for example, a frequency counter.

If portable terminal 1 has a bidirectional communication function, information regarding a skin condition, such as moisture content or sebum content, of the skin may be sent to a server via a network, and cosmetic information suited to user's skin condition may be received from the server.

Figure 3A:
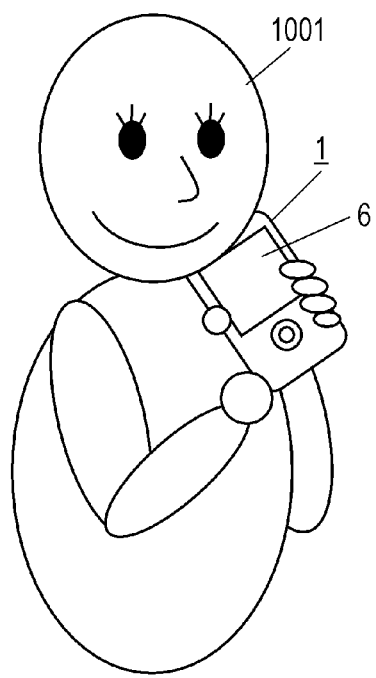
FIG. 3A is a schematic diagram illustrating the portable terminal according to Embodiment 1 in use.

FIG. 3A is a schematic view of portable terminal 1 according to Embodiment 1 used by user 1001 for measuring a skin condition with skin-condition measurement sensor 4. User 1001 measures a skin condition by pressing measurement unit 9 of skin-condition measurement sensor 4 to cause measurement unit 9 to contact or approach, mainly his/her chin or cheek or under an upper arm.

According to Embodiment 1, portable terminal 1 includes measurement unit 9 including comb-shaped electrodes 7 and 8 and located outside display screen 6 on the surface of front plate 5, i.e., on front surface 2A of case 2, as shown in FIG. 1. Comb-shaped electrodes 7 and 8 of measurement unit 9 may be formed on the surface of front plate 5, or under front plate 5. Measurement unit 9 may protrude from front plate 5 (front surface 2A) so as to securely contact the skin. Alternatively, measurement unit 9 may not protrude from front plate 5 (front surface 2A) when measurement unit 9 is not used, and measurement unit 9 may protrudes from front plate 5 (front surface 2A) only when measurement unit 9 is used.

User 1001 may use a protection case covering case 2 to protect portable terminal 1 from impact, or from design preferences. Such a protection case may often have an opening to expose front surface 2A including display screen 6 but cover rear surface 2B. Even if rear surface 2B of case 2 is covered by the protection case, the skin condition can be measured quickly since measurement unit 9 is disposed on front surface 2A that is the surface of front plate 5, and it is not necessary to remove the protection case from case 2.

Case 2 of portable terminal 1 according to Embodiment 1 has long axis Y and short axis X perpendicular to long axis Y, and has a shape that is elongate along long axis Y, as shown in FIG. 1. Case 2 has ends P1 and P2 opposite to each other in a direction along long axis Y. Measurement unit 9 is disposed between display screen 6 and end P1. Since measurement unit 9 is positioned at end P1 of portable terminal 1, when user 1001 presses measurement unit 9 against or brings it close to the skin as shown in FIG. 3A, display screen 6 can be kept away from the skin. Thus, display screen 6 is prevented from being contaminated with sebum or cosmetics.

User 1001 may bond a protection sheet on display screen 6 to protect the display from scratches. Since measurement unit 9 of portable terminal 1 is provided outside display screen 6 according to Embodiment 1, the protection sheet may be bonded only to display screen 6 and can readily be prevented from being bonded on the surface of measurement unit 9. Presence or absence of the protection sheet over measurement unit 9 may affect the capacitance, resistance, or light intensity detected with measurement unit 9 since the sheet changes the distance between measurement unit 9 and the skin. Portable terminal 1 according to Embodiment 1 can thus prevent measurements by measurement unit 9 from being affected by forms of use by user 1001.

Figure 3B:
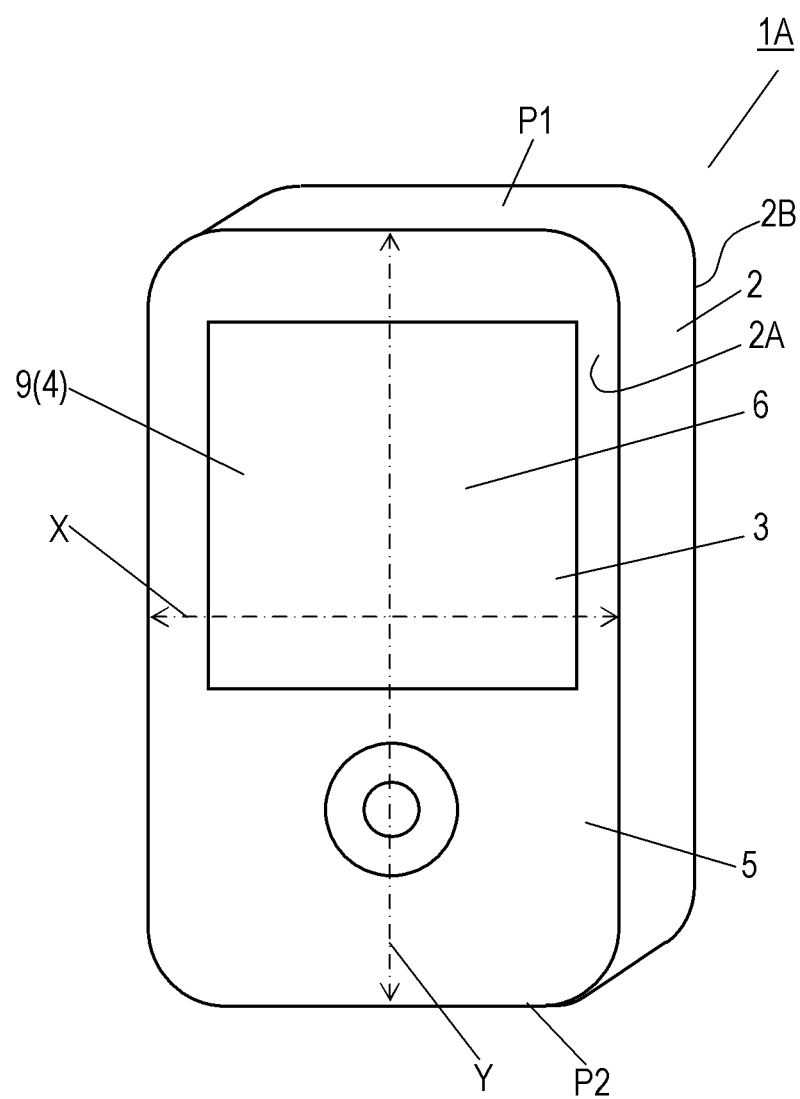
FIG. 3B is a perspective view of another portable terminal 1A according to Embodiment 1.

FIG. 3B is a perspective view of another portable terminal 1A according to Embodiment 1. In FIG. 3B, same components identical to those of portable terminal 1 shown in FIG. 1 are denoted by the same reference numerals. Portable terminal 1A includes skin-condition measurement sensor 4 disposed on front surface 2A of case 2, such that display screen 6, in particular, functions as measurement unit 9 of skin-condition measurement sensor 4.

As described above, as each of portable terminals 1 and 1A according to Embodiment 1 includes skin-condition measurement sensor 4, user 1001 can measure a skin conditions anytime, anywhere at desired timing. Portable terminal 1 also provides advantages of effortless operation and contamination proof of display screen 6.

Exemplary Embodiment 2

Figure 4A:
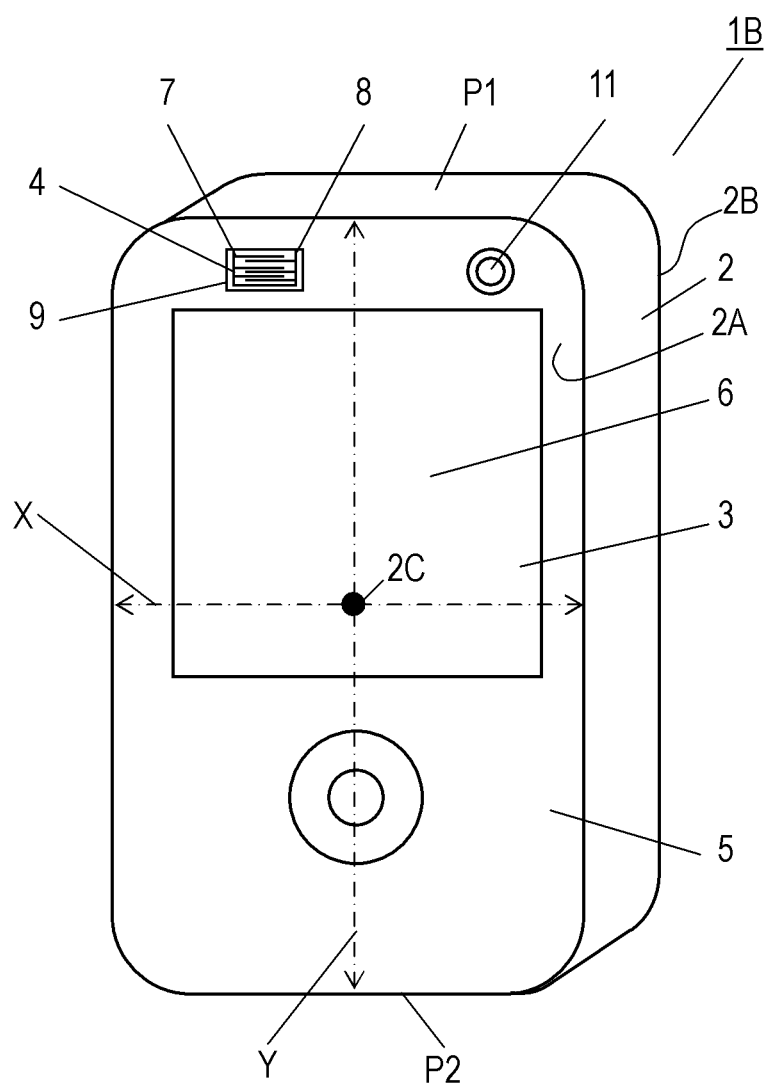
FIG. 4A is a perspective view of a portable terminal according to Exemplary Embodiment 2 of the present invention.
Figure 4B:
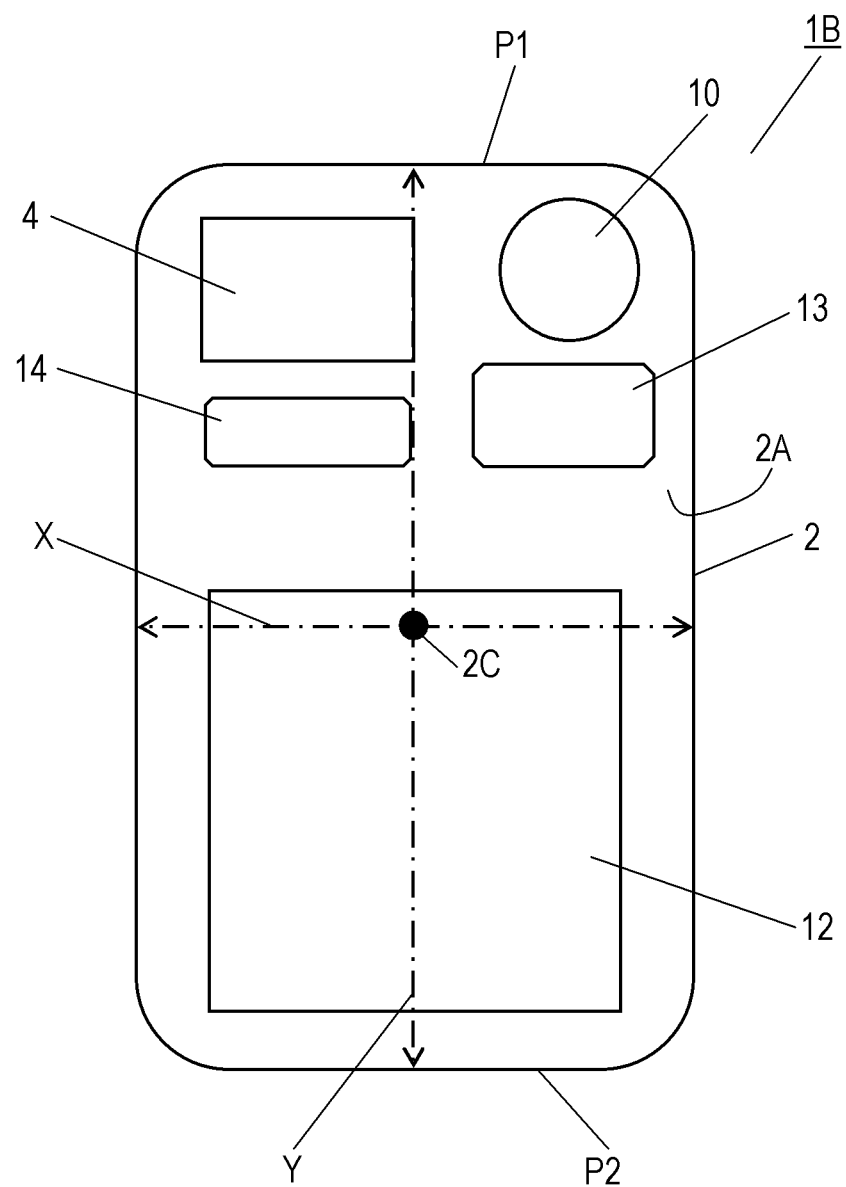
FIG. 4B is a schematic cross-sectional view of the portable terminal according to Embodiment 2.

FIG. 4A is a perspective view of portable terminal 1B according to Exemplary Embodiment 2 of the present invention. FIG. 4B schematically shows a cross section of an inside of case 2 of portable terminal 1B from above. In FIGS. 4A and 4B, components identical to those of portable terminal 1 according to Embodiment 1 shown in FIGS. 1 to 3A are denoted by the same reference numerals. Portable terminal 1B further includes a camera module 10 in addition to portable terminal 1 according to Embodiment 1.

Camera module 10 is accommodated in case 2. Camera module 10 includes imaging lens 11 shown in FIG. 4A. Imagine lens 11 is exposed on a surface of front plate 5, i.e., on front surface 2A of case 2. The phrase, "exposed on a surface of front plate 5" here includes various cases that imaging lens 11 is disposed on the surface of front plate 5, is exposed through transparent front plate 5, or protrudes from front plate 5.

Since imaging lens 11 is exposed in the same plane (front surface 2A) as display screen 6 of display unit 3, the user can take a picture as the user sees his/her own image displayed on display screen 6.

Imaging lens 11 is disposed outside display screen 6 and between display screen 6 and one of both ends P1 and P2 of case 2, in particular, between display screen 6 and end P1, similarly to measurement unit 9.

Portable terminal 1B according to Embodiment 1 allows the user to take a picture of himself/herself since the user faces display screen 6, and also has imaging lens 11 close to measurement unit 9. Therefore, when a skin condition is measured by pressing measurement unit 9 against or bringing it close to the skin, an enlarged image of the skin can be taken with camera module 10. In this way, skin-condition measurement sensor 4 can measure not only physical properties, such as moisture, of the skin but also skin conditions, such as skin texture or skin pigment, that can be determined by analysis of the image, so that the sensor can provide a comprehensive and detailed skin analysis. Camera module 10 is preferably disposed adjacent to skin-condition measurement sensor 4. Measurement unit 9 and imaging lens 11 adjacent to each other can measure the same portion of skin simultaneously.

Battery 12 that drives portable terminal 1B is accommodated in case 2. Battery 12 is a rechargeable battery, for example.

Battery 12 is configured to be biased from center 2C of case 2 toward end P2 when accommodated, i.e., be located closer to end P2 than to end P1. In the direction of long axis Y, end P2 is opposite to end P1 where skin-condition measurement sensor 4 and camera module 10 are accommodated. The user uses portable terminal 1B such that end P1 is an upper side and end P2 is a lower side. Therefore, loading heavy battery 12 near end P2 on the lower side lowers the center of gravity of portable terminal 1B so that it is easier for the user to hold portable terminal 1B.

Plural modules, such as flash 13 used for taking pictures with the camera and loudspeaker 14 used for phone communications and playing music, are mounted to case 2. Battery 12 among these has a large volume and needs a large mounting space. Thus, skin-condition measurement sensor 4 located away from battery 12 allows efficient use of space in case 2.

Figure 5:
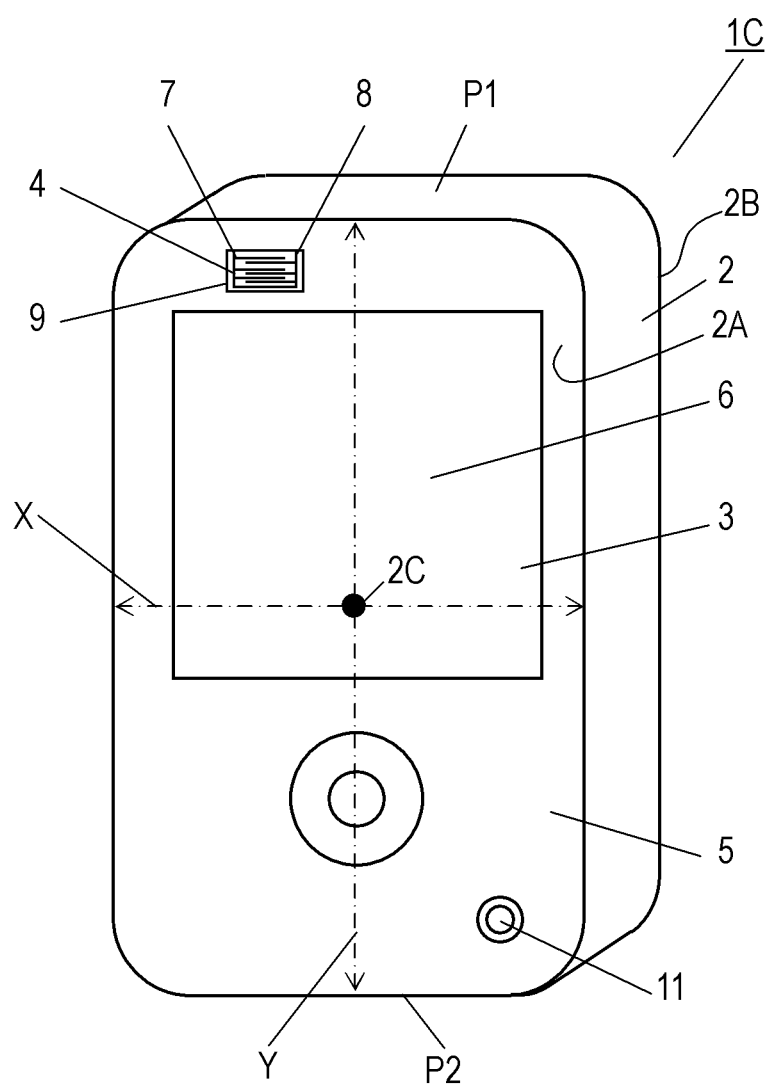
FIG. 5 is a perspective view of another portable terminal according to Embodiment 2.

FIG. 5 is a perspective view of another portable terminal 1C according to Embodiment 2. In FIG. 5, components identical to those of portable terminal 1B shown in FIG. 4A are denoted by the same reference numerals. Portable terminal 1C includes imaging lens 11 of camera module 10 disposed between one of both display screen 6 and one of ends P1 and P2 of case 2, in particular, between end P2 and display screen 6.

Exemplary Embodiment 3

Figure 6A:
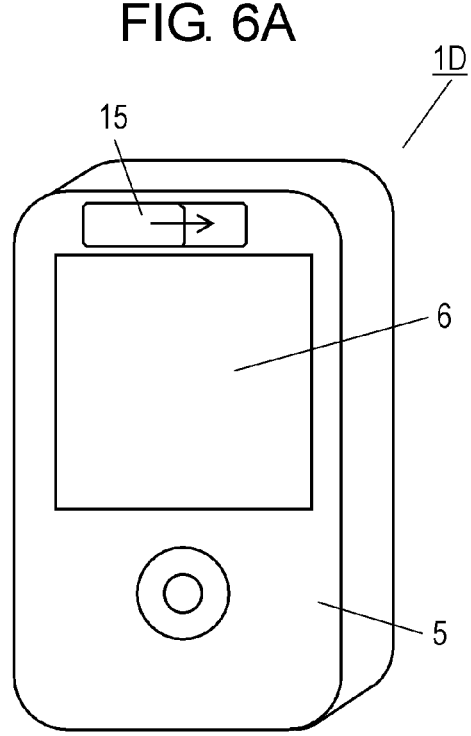
FIG. 6A is a perspective view of a portable terminal according to Exemplary Embodiment 3 of the present invention.
Figure 6B:
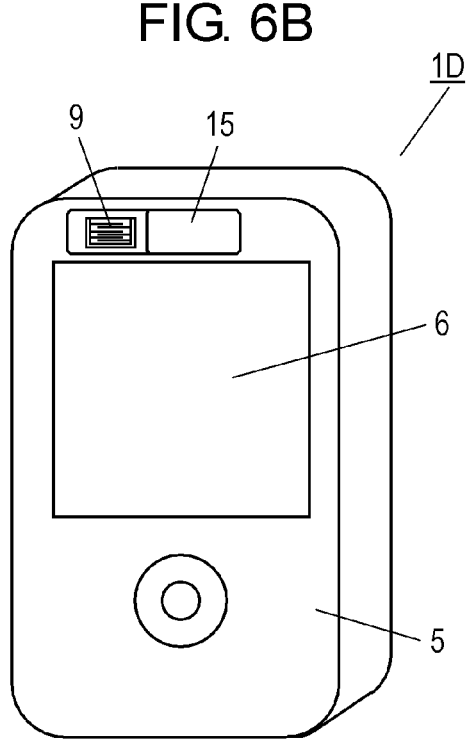
FIG. 6B is a perspective view of the portable terminal according to Embodiment 3.

FIGS. 6A and 6B are perspective views of portable terminal 1D according to Exemplary Embodiment 3. In FIGS. 6A and 6B, components identical to those of portable terminal 1 according to Embodiment 1 shown in FIGS. 1 to 3A are denoted by the same reference numerals. Portable terminal 1D according to Embodiment 3 further includes an auxiliary cover 15 that covers the surface of measurement unit 9.

Auxiliary cover 15 is movable with respect to case 2. Auxiliary cover 15 covers the surface of measurement unit 9 as shown in FIG. 6A except during the measurement of the skin condition. When the skin condition is to be measured, auxiliary cover 15 is slid, as shown in FIG. 6B, or removed, or rotated, to expose measurement unit 9 on the surface of front plate 5, i.e., on front surface 2A of case 2.

Auxiliary cover 15 prevents adhesion of dust or dirt on measurement unit 9 and helps maintain measurement accuracy. Measurement unit 9 securely contacting the skin can also be kept hygienic with auxiliary cover 15.

Exemplary Embodiment 4

Figure 7A:
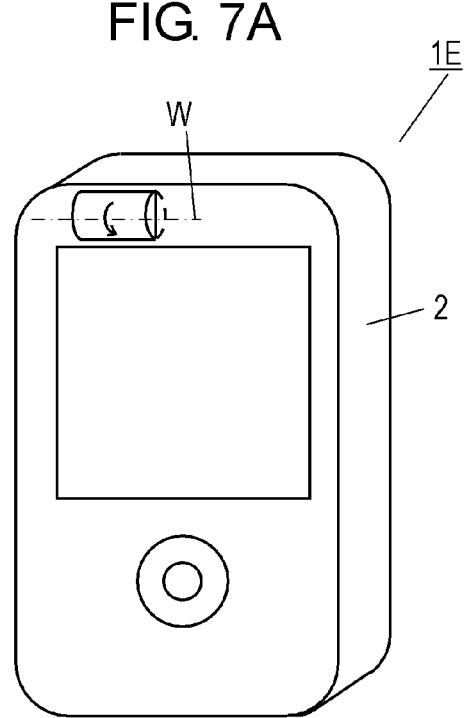
FIG. 7A is a perspective view of a portable terminal according to Exemplary Embodiment 4 of the present invention.
Figure 7B:
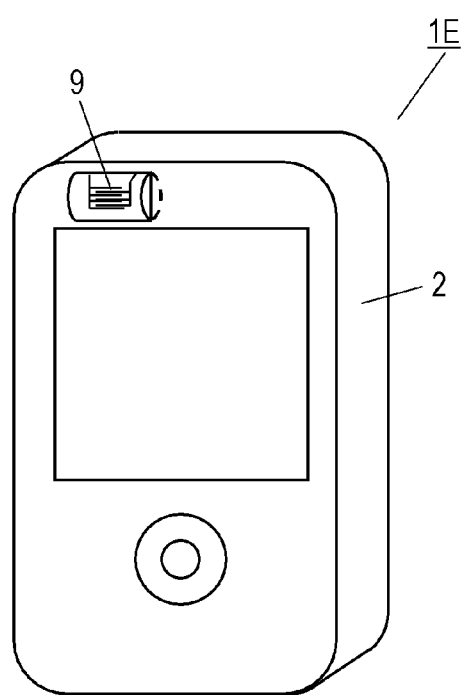
FIG. 7B is a perspective view of the portable terminal according to Embodiment 4.

FIGS. 7A and 7B are perspective views of portable terminal 1E according to Exemplary Embodiment 4. In FIGS. 7A and 7B, components identical to those of portable terminal 1 according to Embodiment 1 shown in FIGS. 1 to 3A are denoted by the same reference numerals. Portable terminal 1E according to Embodiment 4 includes measurement unit 9 that is movable with respect to case 2.

Measurement unit 9 has a measurement surface that faces a skin of the user, either contacting or not contacting the skin, for measuring a skin condition of the user. When the skin condition is not measured, the measurement surface of measurement unit 9 faces inside of case 2 and is not exposed on the surface of front plate 5 (front surface 2A of case 2) as shown in FIG. 7A. When the skin condition is to be measured, measurement unit 9 rotates about axis W parallel to front plate 5 so that the measurement surface of measurement unit 9 can be exposed on the surface of front plate 5, (front surface 2A of case 2), as shown in FIG. 7B.

Measurement unit 9 movable with respect to case 2 prevents adhesion of dust or dirt on measurement unit 9, and hence, helps maintain measurement accuracy. Measurement unit 9 securely contacting the skin can also be kept hygienic.

Since measurement unit 9 is provided on a rotating member, measurement unit 9 protrudes from display screen 6 when the skin condition is measured so that measurement unit 9 can readily contact the skin securely. Since measurement unit 9 entirely contacts the skin securely, measurement accuracy of the skin condition can be improved. Also, since display screen 6 is relatively distanced from the skin, adhesion of skin sebum or the like on display screen 6 can be prevented.

While portable terminals 1, 1A to 1E according to Embodiments 1 to 4 are a high-functionality portable phone, they may be a PHS, PDA, personal computer, portable tool, electronic dictionary, electronic calculator, game device, and the like, instead of the portable phone. A flat plate type portable terminal, in particular, having the display screen on the surface, is even easier for the user to carry and operate.

Exemplary Embodiment 5

Figure 8:
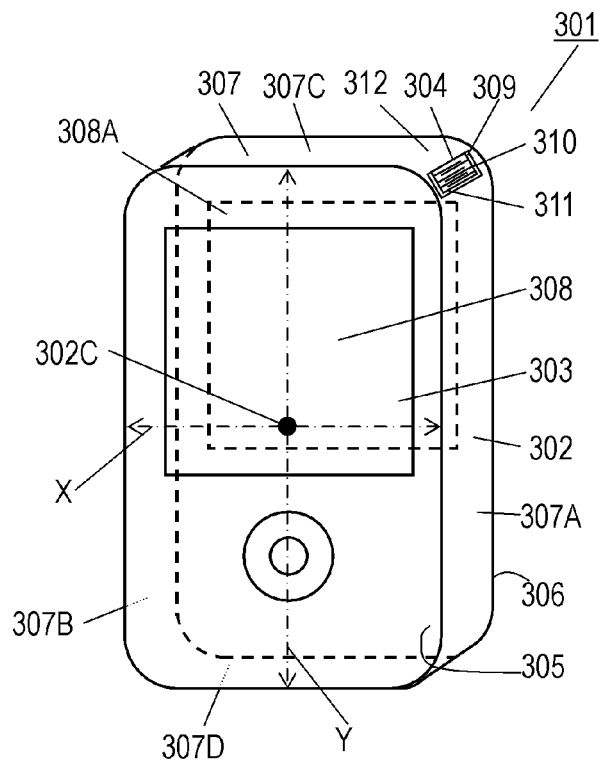
FIG. 8 is a perspective view of a portable terminal according to Exemplary Embodiment 5 of the present invention.

FIG. 8 is a perspective view of portable terminal 301 according to Embodiment 5 of the present invention. Portable terminal 301 is a high-functionality portable phone called as a smart phone.

Portable terminal 301 can be used not only for mutual data communications, such as phone communications or sending/receiving of email, but also for playing or storing media or browsing websites. Portable terminal 301 may be operable for both wireless and wired communications.

As shown in FIG. 8, portable terminal 301 according to Embodiment 5 has substantially a parallelepiped plate shape.

Portable terminal 301 includes case 302, display unit 303 accommodated in case 302, and skin-condition measurement sensor 304 accommodated in case 302.

Case 302 further accommodates therein integrated circuits and other circuits that execute computing operations of portable terminal 301. The integrated circuits and other circuits include microprocessors, memories, a battery for driving portable terminal 301, circuit boards, input/output circuits, and various input/output assistance circuits. Portable terminal 301 includes an antenna. The antenna may be exposed on the outside of case 302, or accommodated inside. The wireless communications may be based on various communication protocols, such as high frequency communications, or Bluetooth™.

Case 302 has substantially a plate shape having front surface 305, rear surface 306 opposite to front surface 305, and side-circumferential surface 307 connected to front surface 305 and rear surface 306 to surround front surface 305 and rear surface 306.

Side-circumferential surface 307 includes side surfaces 307A to 307D. Side surface 307B is opposite to side surface 307A. Side surface 307D is opposite to side surface 307C. Side surface 307C connects one end of side surface 307A and one end of side surface 307B. Side surface 307D connects another end of side surface 307A and another end of side surface 307B.

Side surfaces 307A and 307B are symmetrical to each other with respect to long axis Y passing through center 302C of case 302. Side surfaces 307C and 307D are symmetrical to each other with respect to short axis X passing through center 302C of case 302. Short axis X and long axis Y cross each other perpendicularly at center 302C.

While portable terminal 301 according to Embodiment 5 has side surface 307A and side surface 307B on the right and left, respectively, as shown in FIG. 8, the right and left may be inverted. While side surface 307C and side surface 307D are on upper and lower sides, respectively, as shown in FIG. 8, the up and down may be inverted. Further, side surfaces 307A and 307B may be positioned opposite to each other in the up and down direction in FIG. 8, and side surfaces 307C and 307D may be positioned opposite to each other in the left-right direction in FIG. 8.

Display unit 303 includes, for example, a touchscreen and display screen 308 which is a liquid crystal display, such as an organic liquid crystal display and the like. Display screen 308 is exposed on front surface 305 of case 302. While display screen 308 of portable terminal 301 is exposed on front surface 305 of case 302 according to Embodiment 5, the portable terminal may include display screen 308A that is exposed on rear surface 306, instead of display screen 308. Portable terminal 301 according to Embodiment 5 may further include display screen 308A that is exposed on rear surface 306.

A transparent plate made of glass or acrylic is provided above display screen 308, and made integral with case 302. Display screen 308 is exposed on front surface 305 of portable terminal 301 through the transparent plate. In other words, the user can see display screen 308 through the transparent plate.

Front surface 305 and rear surface 306 of portable terminal 301 has substantially rectangular shapes, but may have square shapes, or may have other polygonal shapes.

Skin-condition measurement sensor 304 includes measurement unit 309 that measures a skin condition, and a detection circuit connected to measurement unit 309. The detection circuit detects electrical signals output from measurement unit 309.

According to Embodiment 5, skin-condition measurement sensor 304 of portable terminal 301 is a moisture sensor that measures moisture content of the skin of the user. Other than moisture, skin-condition measurement sensor 304 may measure various other skin conditions, such as a temperature, a sebum content, color, or brightness.

Skin-condition measurement sensor 304 that is a moisture sensor according to Embodiment 5 calculates the moisture content of the skin based on a capacitance.

The moisture sensor includes, for example, a pair of electrodes 310 and 311 that constitute measurement unit 309. Electrodes 310 and 311 contacting or approaching closely the skin surface changes the dielectric constant between electrodes 310 and 311. The change in the capacitance is detected based on this change in the dielectric constant to calculate the moisture content of the skin.

A condition of the moisture of the skin is largely affected by the moisture content of the skin's horny layer. It is, therefore, preferable to measure a change in the capacitance in a region at a depth of about 20 μm from the skin surface. The measurement depth of the moisture sensor may be adjusted by, for example, controlling an interval between electrodes 310 and 311.

Comb electrodes 310 and 311 have a large capacitance to be detected, so that the capacitance can be detected accurately. Parameters, such as resistance or impedance other than the capacitance between electrodes 310 and 311 may also be used to determine the moisture content of the skin.

Brightness, color, and temperature of the skin may be measured with, e.g. an infrared sensor as skin-condition measurement sensor 304. Sebum content of the skin may be measured with, e.g. an optical sensor as skin-condition measurement sensor 304. The optical sensor applies light to a sampling surface and measures the intensity of light reflected from the surface.

Figure 9:
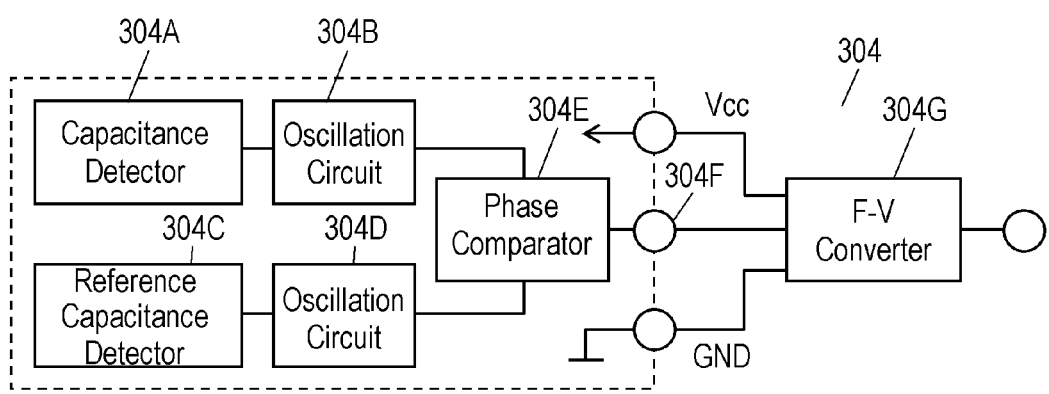
FIG. 9 is a block diagram of a skin-condition measurement sensor of the portable terminal according to Embodiment 5.

FIG. 9 is a block diagram of a capacitive moisture sensor, skin-condition measurement sensor 304 according to Embodiment 5.

Skin-condition measurement sensor 304 includes capacitance detector 304A that detects the moisture content of the skin, and oscillation circuit 304B connected to an output port of capacitance detector 304A to detect the capacitance based on a frequency. Capacitance detector 304A corresponds to measurement unit 309 shown in FIG. 8. Oscillation circuit 304B corresponds to the detection circuit described above.

Figure 10:
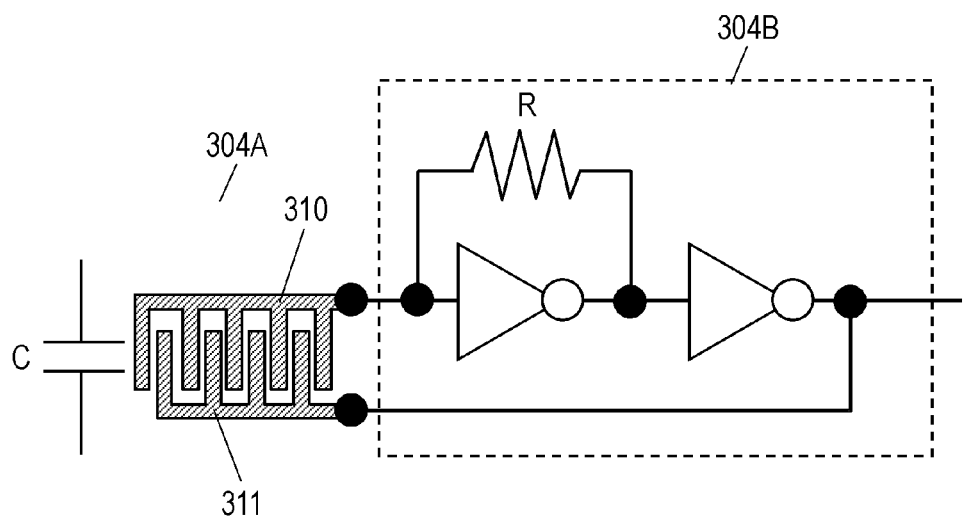
FIG. 10 is a circuit diagram of part of the sensor of the portable terminal according to Embodiment 5.

FIG. 10 is a circuit diagram of skin-condition measurement sensor 304. Specifically, FIG. 10 is a circuit diagram of capacitance detector 304A and oscillation circuit 304B shown in FIG. 9. Oscillation circuit 304B is an RC oscillation circuit (oscillation circuit 304B) having a capacitor formed by electrodes 310 and 311, and resistance R connected to this capacitor either in parallel or in series, and functions as the detection circuit described above.

According to Embodiment 5, as shown in FIG. 9, skin-condition measurement sensor 304 of portable terminal 301 further includes reference capacitance detector 304C that detects a capacitance dependent on ambient conditions, such as temperature and humidity, and oscillation circuit 304D connected to an output port of reference capacitance detector 304C to detect the capacitance based on a frequency.

In skin-condition measurement sensor 304, phase comparator 304E is connected to output ports of oscillation circuits 304B and 304D. Phase comparator 304E detects a difference of output frequencies of oscillation circuits 304B and 304D. Output terminal 304F is connected to an output port of phase comparator 304E. Output terminal 304F is connected to frequency-voltage (F-V) converter 304G.

F-V converter 304G converts a signal representing the difference of the frequencies into an analog voltage. The voltage output from F-V converter 304G can be converted to the moisture content of the skin by a predetermined algorithm since the voltage corresponds to the moisture content. A calculation result of the moisture content of the skin may be displayed on display unit 303 so that the user can realize the moisture content of the skin.

Skin-condition measurement sensor 304 may be operated by a mechanical button or switch mounted in case 2, or from a touchscreen on display screen 308. An operation program may be stored previously in the portable terminal, or may be downloaded by the user via a network.

In skin-condition measurement sensor 304 according to Embodiment 5, direct-current (DC) voltage Vcc supplied from a power source (battery) of portable terminal 301 is supplied via F-V converter 304G to oscillation circuits 304B and 304D constituting the detection circuit.

According to Embodiment 5, the detection circuit of skin-condition measurement sensor 304 includes capacitance detector 304A, oscillation circuit 304B, reference capacitance detector 304C, oscillation circuit 304D, phase comparator 304E, and F-V converter 304G. However, this configuration is just an example, and reference capacitance detector 304C, oscillation circuit 304D, phase comparator 304E, and F-V converter 304G are not essential in the detection circuit. Oscillation circuit 304B may be replaced with other circuit configurations.

For example, accord to Embodiment 5, ambient conditions are measured with a reference capacitance detector 304C separately from measurement unit 309 for measuring moisture content of the skin so as to eliminate an influence of the ambient conditions, such as humidity or temperature. However, it is also possible to measure not only the skin condition but also the ambient conditions only with one measurement unit 309, i.e., only with capacitance detector 304A. In this case, a reference capacitance of an ambient condition may be detected with capacitance detector 304A as an initial value, and a difference from the capacitance measured via the skin may be determined. If the ambient conditions have little influence on measurement, skin-condition measurement sensor 304 may not necessarily include reference capacitance detector 304C, oscillation circuit 304D, and phase comparator 304E.

While portable terminal 301 according to Embodiment 5 detects the capacitance with oscillation circuit 304B, the capacitance may be detected based on a difference in the amplitude instead. In this case, a lock-in amplifier may be used instead of oscillation circuit 304B, for example. While the signal representing a difference in frequency is converted to an analog voltage with F-V converter 304G according to Embodiment 5, the signal may be converted to a bus signal, using, for example, a frequency counter.

If portable terminal 301 has a bidirectional communication function, information regarding the skin condition, such as moisture content or sebum content, of the skin may be sent to a server via a network, and cosmetic information suited to user's skin condition may be received from the server.

Figure 11:
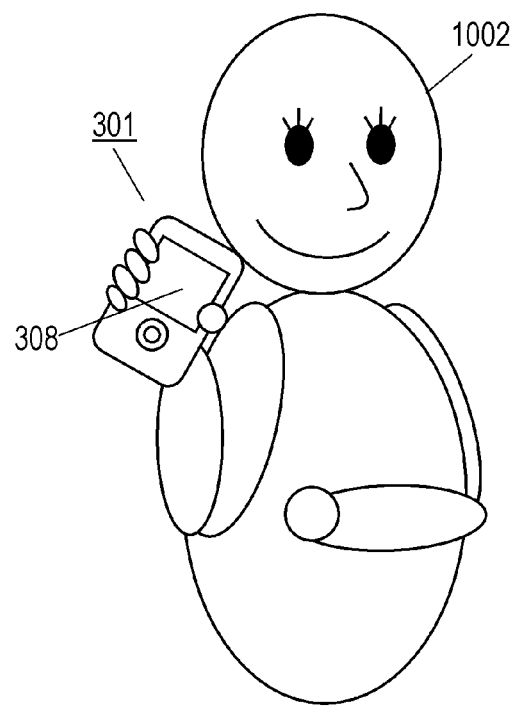
FIG. 11 is a schematic view of the portable terminal according to Embodiment 5 in use.

FIG. 11 is a schematic view of portable terminal 301 according to Embodiment 5 used by user 1002 measuring a skin condition with skin-condition measurement sensor 304. User 1002 measures the skin condition by bringing measurement unit 309 of skin-condition measurement sensor 304 close to, or pressing it tightly against, mainly his/her chin or cheek or under the upper arm.

According to Embodiment 5, measurement unit 309 is provided at corner 312 of case 302. Corner 312 may be right-angled, or may be a curved surface curved from side surface 307A to side surface 307C while protruding outward, as shown in FIG. 8.

Figure 12:
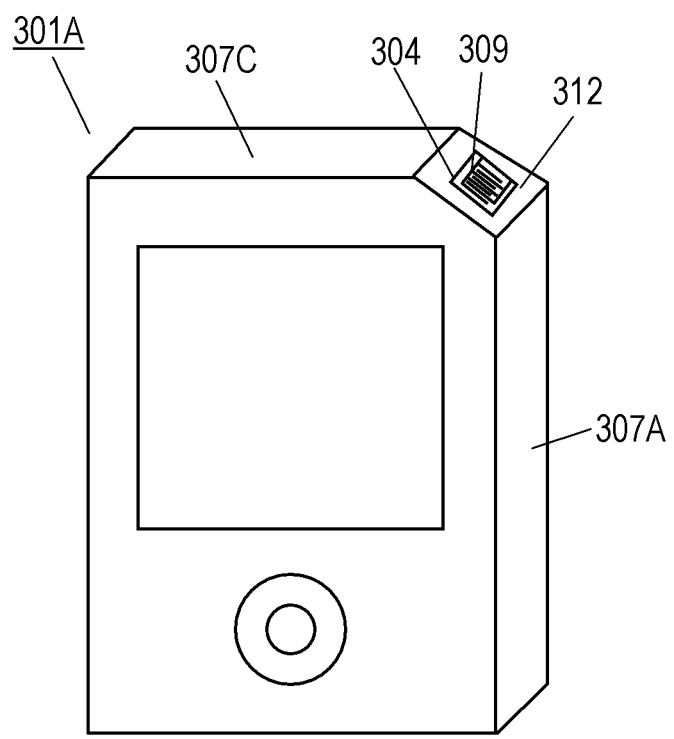
FIG. 12 is a perspective view of another portable terminal according to Embodiment 5.

FIG. 12 is a perspective view of portable terminal 301A according to Embodiment 5. In FIG. 12, components identical to those of portable terminal 301 shown in FIGS. 8 to 11 are denoted by the same reference numerals. In portable terminal 301A shown in FIG. 12, corner 312 is constituted by an inclining surface extending from side surface 307A to side surface 307C inclining inward.

Skin-condition measurement sensor 304 can provide precise measurement with little measurement errors if measurement unit 309 is entirely and evenly brought close to or into tight contact with the skin.

If measurement unit 309 is to be used closely to the skin, and if measurement unit 309 is provided at corner 312, measurement unit 309 can readily be close to, for example, the skin in a recessed area under the chin or on the neck since corner 312 has a small area. Therefore, measurement errors can be reduced because measurement unit 309 is entirely and evenly close to the skin.

In a case that measurement unit 309 is used to securely contact the skin, measurement unit 309 can readily contact the skin securely if, as shown in FIG. 11, user 1002 holds case 302 of portable terminal 301 as a grip part of skin-condition measurement sensor 304. In other words, since measurement unit 309 is provided at corner 312 with a small area, a force from the grip part can easily concentrate thereto, so that measurement unit 309 can readily contact the skin securely. Therefore, measurement errors can be reduced because measurement unit 309 is entirely and evenly contact the skin.

While corner 312 may be right-angled, a curved surface or a flat, inclining surface allows measurement unit 309 to be close to or securely contact the skin entirely and evenly, and have a soft touch to the skin.

Portable terminal 301 according to Embodiment 5 includes measurement unit 309 on the surface of corner 312. Measurement unit 309 may protrude from the surface of corner 312, so that measurement unit 309 can readily contact the skin securely. Alternatively, measurement unit 309 may be provided at corner 312 to be recessed from the surface. This can effectively be applied to the case where measurement unit 309 is close to but spaced a certain distance from the skin since the certain distance can be kept stably.

While portable terminal 301 according to Embodiment 5 has a rectangular cross section parallel to front surface 302A of case 302 (display screen 308), portable terminal 301 may have other polygonal shapes, such as a pentagonal or hexagonal shape. In this case, too, measurement unit 309 may be provided at a corner between adjacent sides, and the corner may have a curved surface.

Portable terminal 301 according to Embodiment 5 includes skin-condition measurement sensor 304 accommodated in case 302 of portable terminal 301 and enables the user of portable terminal 301 to conveniently measure the skin condition anytime, anywhere.

Portable terminal 301 according to Embodiment 5 has display screen 308 (308A) of display unit 303 on front surface 305 or rear surface 306 of case 302, and measurement unit 309 on side-circumferential surface 307. Therefore, even if measurement unit 309 contacts the skin securely, display screen 308 is kept away from the skin, so that display screen 308 is prevented from being contaminated with skin sebum or cosmetics.

The user may bond a protection sheet on display screen 308 to protect the display from scratches. According to Embodiment 5, measurement unit 309 is provided on side-circumferential surface 307 of display screen 308, hence preventing the protection sheet from being bonded on the surface of measurement unit 309. Presence or absence of a protection sheet over measurement unit 309 may affect the capacitance, resistance, or light intensity detected by measurement unit 309 since the sheet changes the distance between measurement unit 309 and the skin. According to Embodiment 5, measurements by measurement unit 309 can thus be prevented from being affected by usage thereof by the user.

Figure 13:
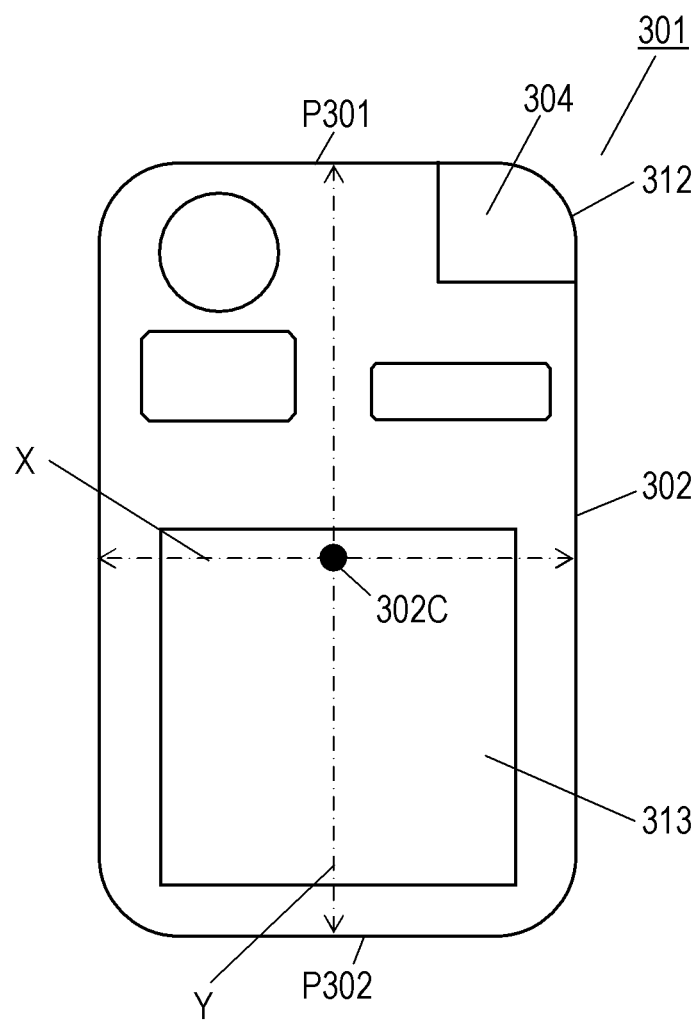
FIG. 13 is a schematic cross-sectional view of the portable terminal according to Embodiment 5.

FIG. 13 is a schematic cross-sectional view of portable terminal 301. Case 302 has ends P301 and P302 opposite to each other in a direction along long axis Y. Skin-condition measurement sensor 304 is provided at corner 312 closer to end P301 than center 302C of case 302. Battery 313 is configured to be located at a position deviating from center 302C of case 302 toward end P302. In other words, skin-condition measurement sensor 304 is located closer to end P301 than to end P302 of case 302, while battery 313 is located closer to end P302 than to end P301 of case 302.

Since battery 313 has a large volume, skin-condition measurement sensor 304 located away opposite to battery 313 allows efficient use of an available space in case 302. In addition, since battery 313 is heavy, skin-condition measurement sensor 304 located opposite to heavy battery 313 provides a preferable weight balance to case 302 and allows user 1002 to readily hold case 302.

While each of portable terminals 301 and 301A has one case 302 according to Embodiment 5, the case may be composed of plural housings connected to each other.

Figure 14A:
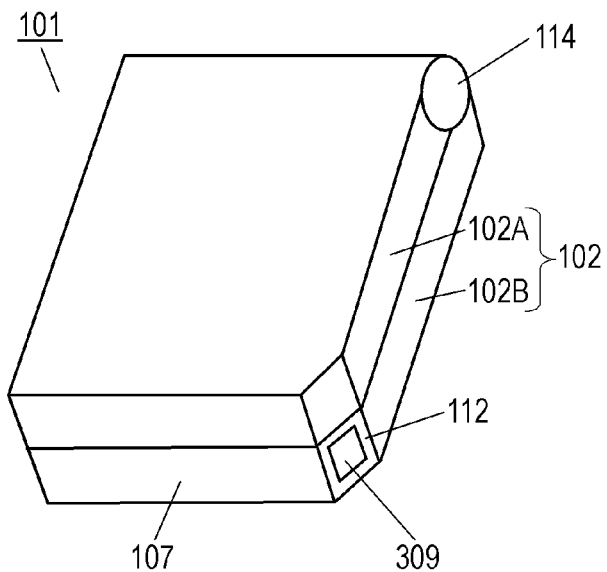
FIG. 14A is a perspective view of still another portable terminal according to Embodiment 5.
Figure 14B:
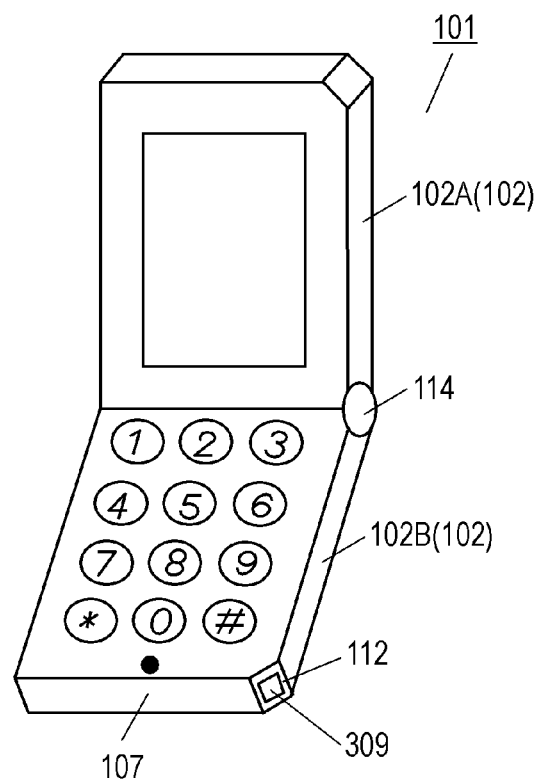
FIG. 14B is a perspective view of the portable terminal shown in FIG. 14A.

FIGS. 14A and 14B are perspective views of further portable terminal 101 according to Embodiment 6. In FIGS. 14A and 14B, components identical to those of portable terminal 301 shown in FIG. 8 to FIG. 11 are denoted by the same reference numerals. Portable terminal 101 is a foldable type. Portable terminal 101 has case 102 instead of case 302 of portable terminal 301 shown in FIGS. 8 to 11. Case 102 includes housings 102A and 102B and hinge 114 that connects housings 102A and 102B. Measurement unit 309 is located at corner 112 of side-circumferential surface 107 of at least one of housings 102A and 102B. Measurement unit 309 of portable terminal 101 can evenly contact or approach the skin of the user, similarly to portable terminal 301.

Figure 15A:
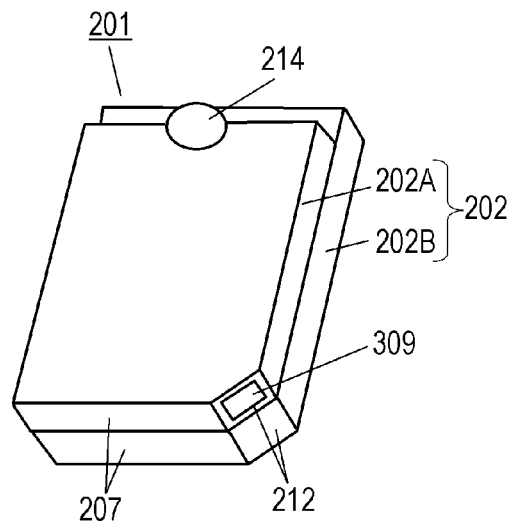
FIG. 15A is a perspective view of further portable terminal according to Embodiment 5.
Figure 15B:
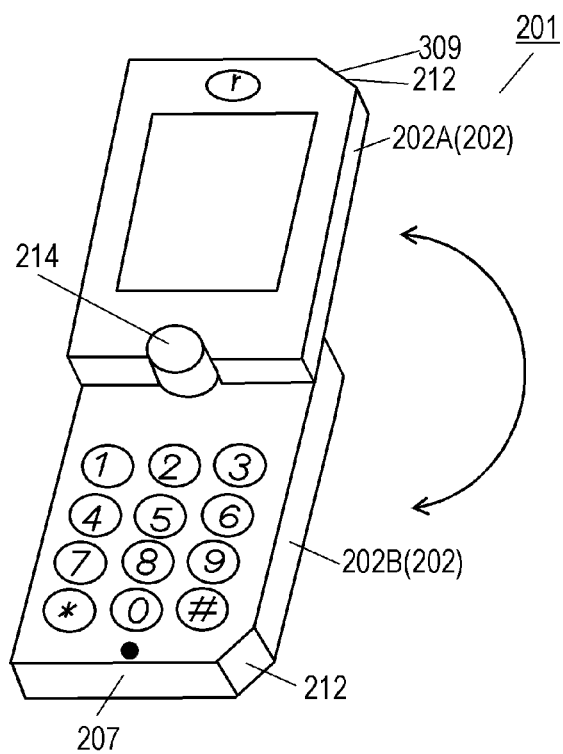
FIG. 15B is a perspective view of the portable terminal shown in FIG. 15A.

FIGS. 15A and 15B are perspective views of further portable terminal 201 according to Embodiment 5. In FIGS. 15A and 15B, components identical to those of portable terminal 301 shown in FIGS. 8 to 11 are denoted by the same reference numerals. Portable terminal 201 is a slidable type. Portable terminal 201 has case 202 instead of case 302 of portable terminal 301 shown in FIGS. 8 to 11. Case 202 includes housings 202A and 202B and rotation shaft part 214 that connects housings 202A and 202B. Housing 202A rotates about rotation shaft part 214 with respect to housing 202B. Measurement unit 309 is located at corner 212 of side-circumferential surface 207 of at least one of housings 202A and 202B. Measurement unit 309 of portable terminal 201 can evenly contact or approach the skin of the user, similarly to portable terminal 301.

Exemplary Embodiment 6

Figure 16A:
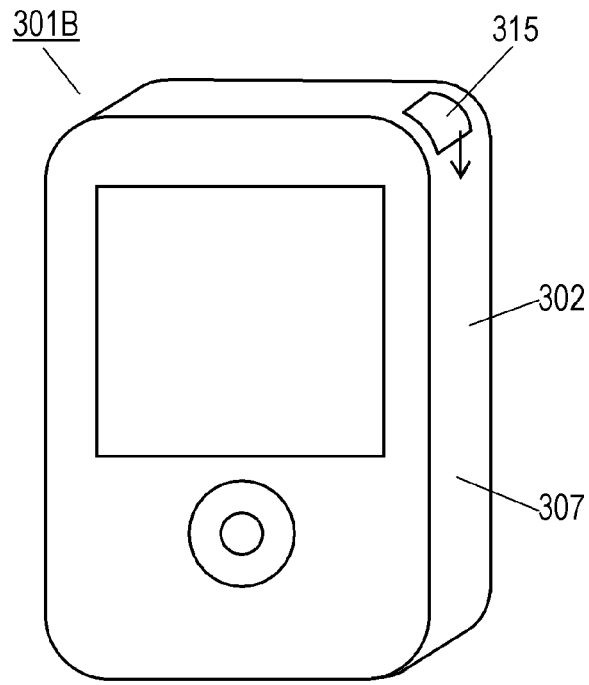
FIG. 16A is a perspective view of a portable terminal according to Exemplary Embodiment 6 of the present invention.
Figure 16B:
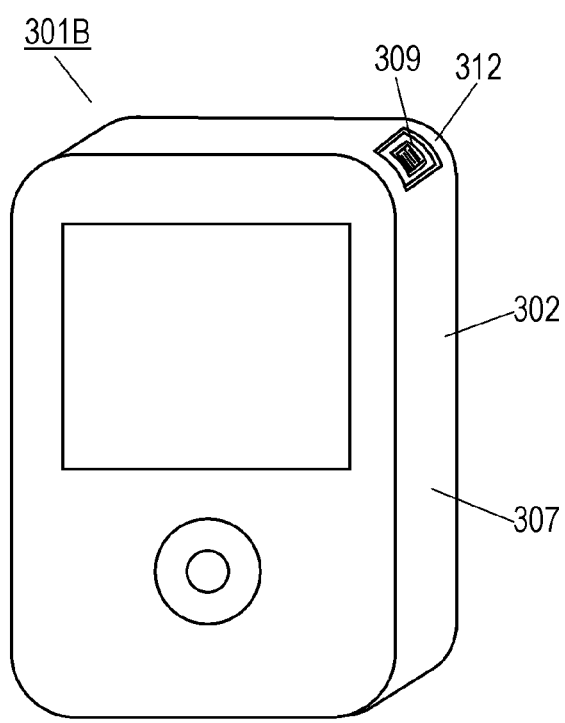
FIG. 16B is a perspective view of the portable terminal according to Embodiment 6.

FIGS. 16A and 16B are perspective views of portable terminal 301B according to Exemplary Embodiment 6. In FIGS. 16A and 16B, components identical to those of portable terminal 301 according to Embodiment 5 shown in FIG. 8 are denoted by the same reference numerals. Portable terminal 301B according to Embodiment 6 further includes an auxiliary cover 315 that can cover the surface of measurement unit 309 of portable terminal 301 according to Embodiment 5.

Auxiliary cover 315 is movable with respect to case 302. Auxiliary cover 315 covers the surface of measurement unit 309 as shown in FIG. 16A except during measurement of the skin condition. When the skin condition is measured, auxiliary cover 315 is slid, as shown in FIG. 16B, or removed, or rotated, to expose measurement unit 309 on the surface of corner 312.

Auxiliary cover 315 prevents adhesion of dust or dirt on measurement unit 309 and helps maintain measurement accuracy. Measurement unit 309 that securely contacts the skin can be kept hygienic.

Exemplary Embodiment 7

Figure 17A:
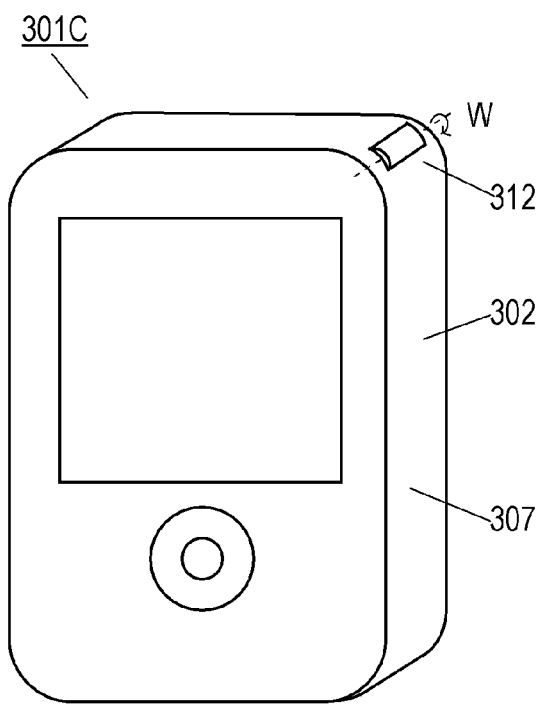
FIG. 17A is a perspective view of a portable terminal according to Exemplary Embodiment 7 of the present invention.
Figure 17B:
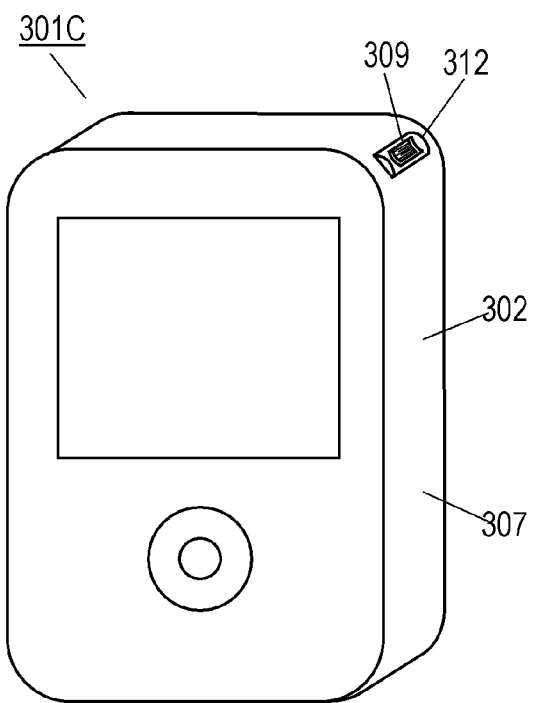
FIG. 17B is a perspective view of the portable terminal according to Embodiment 7.

FIGS. 17A and 17B are perspective views of portable terminal 301C according to Embodiment 7. In FIGS. 17A and 17B, components identical to those of portable terminal 301 according to Embodiment 5 shown in FIG. 8 are denoted by the same reference numerals. Portable terminal 301C according to Embodiment 7 includes measurement unit 309 movable with respect to case 302.

When the skin condition is not measured, the measurement surface of measurement unit 309 faces inside of case 302 and is not exposed on the surface of corner 312 of case 302 as shown in FIG. 17A. When the skin condition is to be measured, measurement unit 309 is rotated about rotation axis W parallel to a width direction of side-circumferential surface 307 to be exposed on the surface of corner 312, as shown in FIG. 17B.

Since measurement unit 309 is movable with respect to case 302, adhesion of dust or dirt on measurement unit 309 is prevented, which helps maintain measurement be accurate. Measurement unit 309 that securely contact the skin can also be kept hygienic.

Since measurement unit 309 is provided on a rotating member, measurement unit 309 protrudes from the surface of corner 312 when the skin condition is measured so that measurement unit 309 can readily contact the skin securely. Since measurement unit 309 entirely contacts the skin, accuracy in measurement of skin conditions can be improved.

While the portable terminals according to Embodiments 5 to 7 are high-functionality portable phones, the portable terminals may be PHSs, PDAs, personal computers, portable tools, electronic dictionaries, electronic calculators, or game devices instead of the portable phones.

Exemplary Embodiment 8

Figure 18:
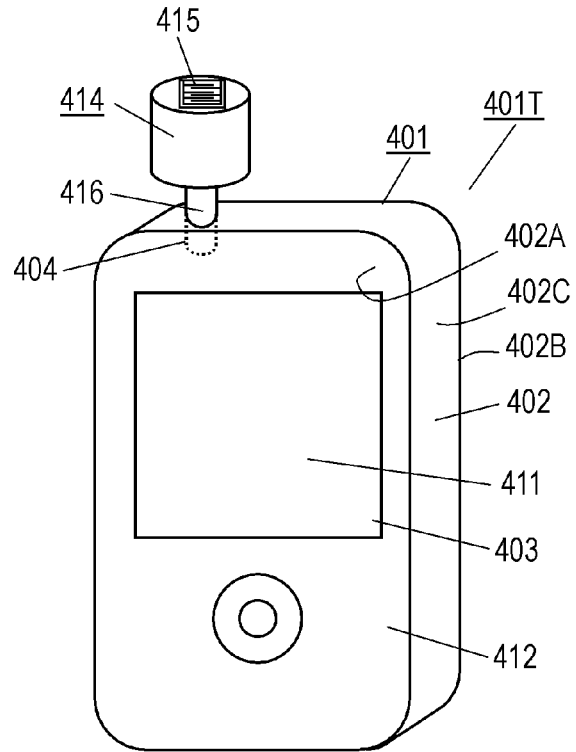
FIG. 18 is a perspective view of a portable terminal according to Exemplary Embodiment 8 of the present invention.

FIG. 18 is a perspective view of portable terminal 401T according to Exemplary Embodiment 8 of the present invention. Portable terminal 401T includes portable terminal (portable terminal body) 401 and skin-condition measurement device 414. Portable terminal (portable terminal body) 401 is a high-functionality portable phone commonly called as a smart phone.

Portable terminal 401 can be used not only for mutual data communications, such as phone communications or sending/receiving of email, but also for playing or storing media or browsing websites. This portable terminal may be operable for both wireless and wired communications. The wireless communications may be based on various communication protocols, such as high frequency communications, Bluetooth™.

As shown in FIG. 18, portable terminal 401 includes case 402 and display unit 403 accommodated in case 402. Case 402 has substantially a plate shape having front surface 402A, rear surface 402B opposite to front surface 402A, and side-circumferential surface 402C connected to front surface 402A and rear surface 402B to surround front surface 402A and rear surface 402B. Case 402 may not necessarily have a flat plate shape, but may be a folded type, or may have various other shapes, such as spherical. Skin-condition measurement device 414 includes measurement unit 415 that measures a skin condition of a user, a detection circuit that processes signals from measurement unit 415, and plug 416.

Case 402 has a cavity provided therein. Display unit 403 is accommodated in this cavity. Earphone jack 404 is provided on side-circumferential surface 402C of case 402. While earphone jack 404 is located above display unit 403 according to Embodiment 8, earphone jack 404 may be located below, or on one side of, display unit 403. Earphone jack 404 may be provided in rear surface 402B of case 402.

Figure 19:
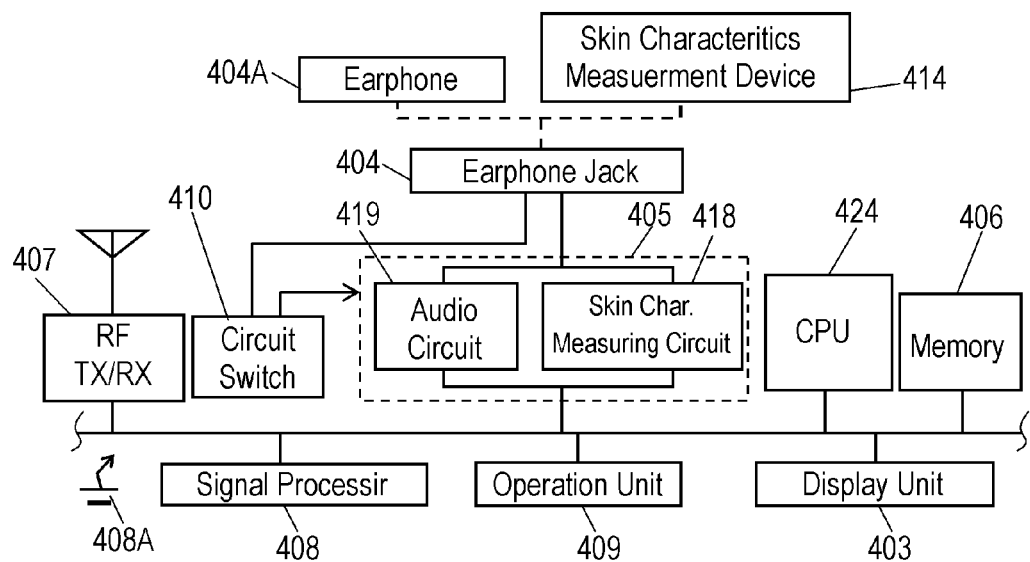
FIG. 19 is a circuit block diagram of the portable terminal according to Embodiment 8.

FIG. 19 is a circuit block diagram of portable terminal 401. Case 402 accommodates, in the cavity, display unit 403, interface unit 405, memory unit 406, radio frequency (RF) transmitter/receiver 407, signal processor 408, operation unit 409, circuit switch unit 410, and central processing unit (CPU) 424. Battery 408A that drives portable terminal 401 is configured to be accommodated in the cavity of case 402. Earphone jack 404 is configured to receive earphone 404A connected thereto, as well as plug 416 of skin-condition measurement device 414 connected thereto. Earphone 404A may not necessarily be an earphone, but may be a stereo headphone, earphone microphone, or any of various other devices that output sound in response to an electrical signal input thereto.

Display unit 403 includes, e.g. a touchscreen and display screen 411 which is a liquid crystal display, such as an organic liquid crystal display.

Case 402 has an opening covered by front plate 412. Front plate 412 where display screen 411 is located has a transparent plate portion made of glass or acrylic. Display screen 411 is exposed on front surface 402A of case 402 through front plate 412. In other words, the user can see display screen 411 through transparent front plate 412.

Figure 20:
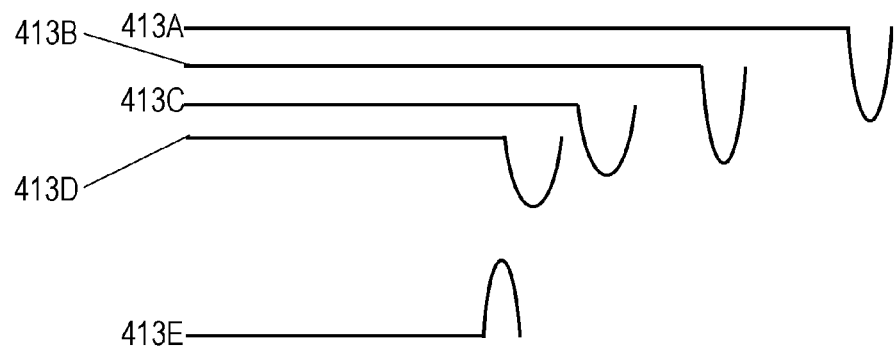
FIG. 20 is a schematic diagram of an earphone jack of the portable terminal according to Embodiment 8.

FIG. 20 is a schematic diagram of earphone jack 404 of portable terminal 401. Earphone jack 404 includes plural contacts 413A to 413E. According to Embodiment 8, four of contacts 413A to 413D are used while contact 413E is idle and not connected to anything. Specifically, contacts 413A and 413B function as a voltage supply and a ground point, respectively. Contacts 413C and 413D function as data lines.

Figure 21:
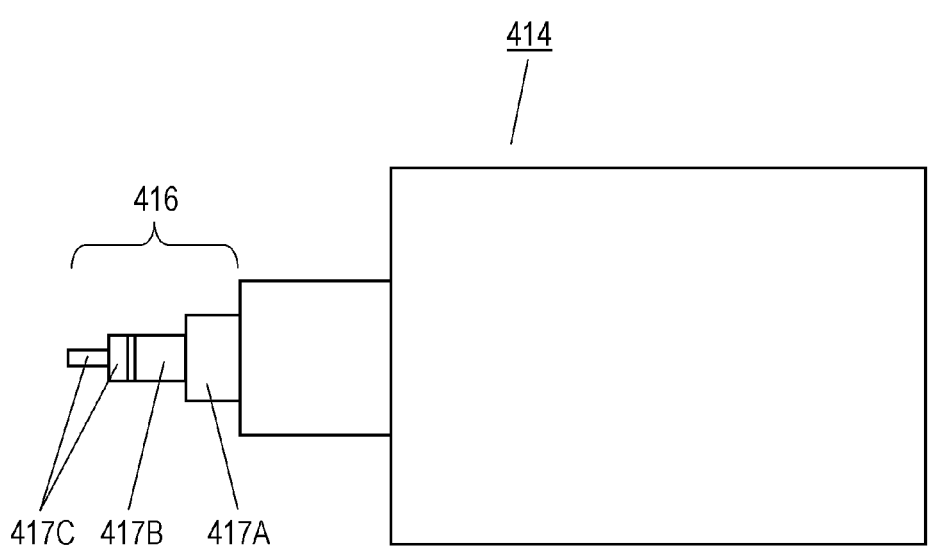
FIG. 21 is a plan view of a skin-condition measurement device of the portable terminal according to Embodiment 8.

FIG. 21 is a plan view of skin-condition measurement device 414. Plug 416 includes three contacts 417A to 417C. Contacts 417A, 417B, and 417C function as a voltage supply, ground point, and data line, respectively.

When plug 416 is inserted into and connected to earphone jack 404 of portable terminal 401 shown in FIG. 20, contact 417A of voltage-supply and contact 417B of grounding of plug 416 contact and are electrically connected with contact 413A of voltage-supply and contact 413B of grounding of earphone jack 404, respectively, while contact 417C of the data line of plug 416 contacts and is electrically connected with both contacts 413C and 413D of the data lines of earphone jack 404.

That is, skin-condition measurement device 414 is mechanically and electrically connected to portable terminal 401 when plug 416 is inserted into earphone jack 404. When skin-condition measurement device 414 is electrically connected to portable terminal 401, power is supplied to skin-condition measurement device 414 from battery 408A of portable terminal 401. Skin condition data are transmitted from skin-condition measurement device 414 and received by portable terminal 401 as an electrical signal.

A plug of earphone 404A, which is a stereo headphone or an earphone microphone, is often connected to earphone jack 404. Therefore, as shown in FIG. 19, interface unit 405 connected to earphone jack 404 includes skin-condition measurement circuit 418 and audio circuit 419. Skin-condition measurement circuit 418 is designed to process electrical signals representing the skin condition. Audio circuit 419 is designed to process electrical signals representing sound.

When plug 416 of skin-condition measurement device 414 is inserted into earphone jack 404 of portable terminal 401, circuit switch unit 410 shown in FIG. 19 detects the inserted device, automatically selects skin-condition measurement circuit 418, and switches the connection of the circuit.

When skin-condition measurement circuit 418 is selected, operation unit 409 of portable terminal 401 which may be operation buttons or a touchscreen functions as operation unit 409 of skin-condition measurement device 414. If operation is made via a touchscreen, an operation program (application) for skin-condition measurement device 414 which may be previously downloaded via a network and stored in memory unit 406 start up. Skin condition measurement signals sent from skin-condition measurement device 414 to portable terminal 401 can be displayed on display unit 403.

A resistance between contacts 417A to 417C of plug 416, for example, is measured to determine whether plug 416 connected to earphone jack 404 is that of skin-condition measurement device 414 or a stereo headphone or an earphone microphone.

Figure 22:
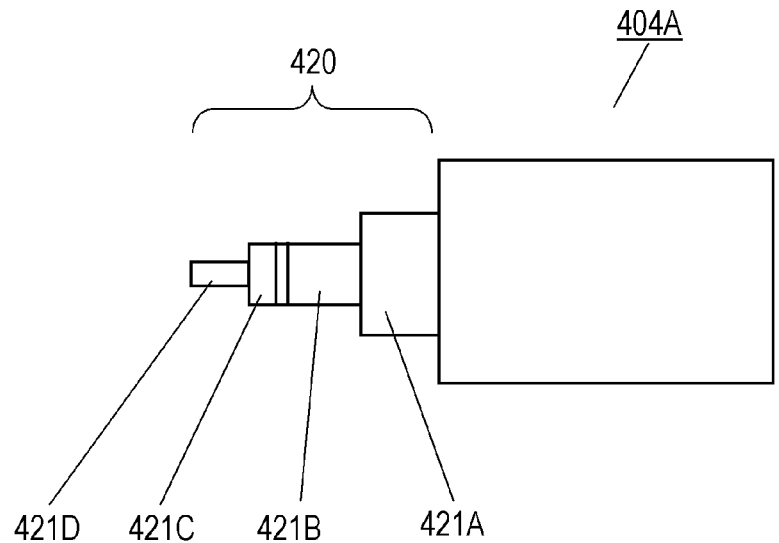
FIG. 22 is a plan view of an earphone plug of the portable terminal according to Embodiment 8.

FIG. 22 is a plan view of plug 420 of earphone 404A of portable terminal 401 according to Embodiment 8. Earphone 404A is an earphone microphone. Plug 420 has four contacts, contact 421A functioning as a voltage supply, contact 421B as a ground point, contact 421C as an earphone terminal, and contact 421D as a microphone terminal.

On the other hand, as shown in FIG. 21, plug 416 of skin-condition measurement device 414 has contact 417C that functions as a data line corresponding to contact 421C, and contact 421D which is the microphone terminal of earphone 404A shown in FIG. 22. Contacts 417B and 417A that are the ground point and voltage supply of skin-condition measurement device 414 shown in FIG. 21 are located at the same positions as contacts 421B and 421A that are the ground point and voltage supply of earphone 404A shown in FIG. 22, respectively. In other words, when plug 420 of earphone 404A is inserted into earphone jack 404 to connect earphone 404A to earphone jack 404, contacts 421A to 421D of plug 420 contact and are electrically connected to contacts 413A to 413D of earphone jack 404, respectively.

As described above, when plug 420 of earphone 404A is inserted, the resistance between contacts 421C and 421B that are the earphone terminal and ground point of earphone 404A is different from the resistance between contacts 421D and 421B that are the microphone terminal and ground point. On the other hand, in the case that skin-condition measurement device 414 is inserted, the resistance between contact 417C that corresponds to the earphone terminal and contact 417B that is the ground point is the same as the resistance between contact 417C that corresponds to the microphone terminal and contact 417B that is the ground point since the resistance is measured between the same data line and ground point. Accordingly, if the resistance detected between contacts 413C and 413D of earphone jack 404 is the same as the resistance between 413C and 413E, circuit switch unit 410 can determine that skin-condition measurement device 414 is connected to earphone jack 404. Alternatively, if circuit switch unit 410 detects that contacts 413D and 413E of earphone jack 404 are electrically connected, it can determine that skin-condition measurement device 414 is connected to earphone jack 404. There are various other algorithms for switching over circuits. For example, the resistance between contacts 417C and 417B that are the data line and ground point may be determined to be different from that of earphone 404A to distinguish the case that skin-condition measurement device 414 is connected.

According to Embodiment 8, skin-condition measurement device 414 is a moisture sensor that measures the moisture content of the skin of the user. Other than moisture, skin-condition measurement device 414 may measure various other skin conditions, such as temperature, sebum content, color, or brightness.

The moisture sensor that is skin-condition measurement device 414 according to Embodiment 8 calculates the moisture content of the skin based on a capacitance.

The skin-condition measurement device 414 includes, for example, a pair of electrodes 422 and 423 constituting measurement unit 415. Upon contacting or approaching a skin surface, electrodes 422 and 423 has the dielectric constant between electrodes 422 and 423 change. The rate of change in the dielectric constant between electrodes 422 and 423 is detected based on a change in a frequency to measure a change in the capacitance between electrodes 422 and 423.

The condition of moisture of skin is largely affected by the moisture content of a horny layer of the skin. It is, therefore, preferable to measure a change in the capacitance in a region at a depth of about 20 μm from the skin surface. The measurement depth of the moisture sensor may be adjusted, for example, by controlling the interval between electrodes 422 and 423.

Electrodes 422 and 423, upon being comb-shaped electrodes, can detect a large capacitance, so that the capacitance can be measured accurately. Parameters, such as a resistance or impedance, other than the capacitance between electrodes 422 and 423 may be used to determine the moisture content of the skin.

Brightness, color, and temperature of the skin can be measured with, e.g. an infrared sensor as skin-condition measurement device 414. Sebum content of the skin can be measured with, e.g. an optical sensor as skin-condition measurement device 414. The optical sensor applies light to a sampling surface and measures the intensity of light reflected from the surface.

Figure 23:
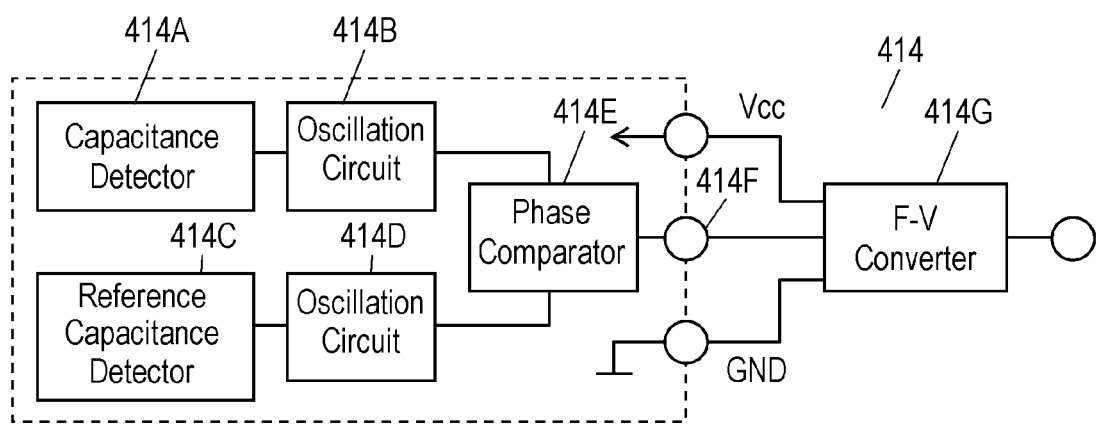
FIG. 23 is a block diagram of the skin-condition measurement device of the portable terminal according to Embodiment 8.

FIG. 23 is a block diagram of a capacitive moisture sensor that is skin-condition measurement device 414.

Skin-condition measurement device 414 includes capacitance detector 414A that detects the moisture content of the skin, and oscillation circuit 414B connected to an output side of capacitance detector 414A and detecting the capacitance based on a frequency. Capacitance detector 414A corresponds to measurement unit 415 shown in FIG. 18.

Figure 24:
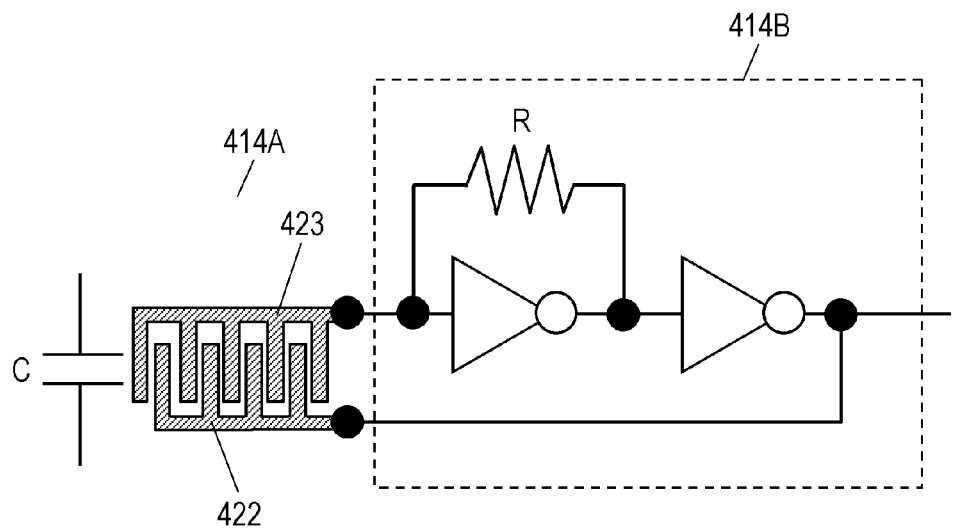
FIG. 24 is a circuit diagram of the skin-condition measurement device according to Embodiment 8.

FIG. 24 is a circuit diagram of skin-condition measurement device 414. Specifically, FIG. 24 is a circuit diagram of capacitance detector 414A and oscillation circuit 414B shown in FIG. 19. Oscillation circuit 414B is an RC oscillation circuit including a capacitor formed by the pair of electrodes 422 and 423 mentioned above, and resistance R connected in parallel or in series, and functions as the detection circuit.

As shown in FIG. 23, skin-condition measurement device 414 further includes reference capacitance detector 414C that detects ambient conditions, such as temperature and humidity, and oscillation circuit 414D connected to an output port of reference capacitance detector 414C to detect the capacitance based on a frequency.

Phase comparator 414E is connected to output ports of oscillation circuits 414B and 414D. Phase comparator 414E detects a difference in output frequencies of oscillation circuits 414B and 414D. Output terminal 414F is connected to an output port of phase comparator 414E. Output terminal 414F is connected to frequency-voltage (F-V) converter 414G.

F-V converter 414G converts a signal representing the difference in the frequencies into an analog voltage. The voltage output from F-V converter 414G is output to the data line of plug 416. The output voltage can be converted to the moisture content of the skin by a predetermined algorithm since the output voltage corresponds to the moisture content. The calculation result of the moisture content of the skin may be displayed on display unit 403 so that the user can realize the moisture content of the skin.

In the moisture sensor that is skin-condition measurement device 414 according to Embodiment 8, DC voltage Vcc supplied from the voltage supply of plug 416 is supplied via F-V converter 414G to oscillation circuits 414B and 414D constituting the detection circuit. The detection signal from the detection circuit is output to the data line via F-V converter 414G. The detection circuit is further connected to a ground point via F-V converter 414G.

Skin-condition measurement device 414 according to Embodiment 8 measures humidity and temperature with a reference capacitance detector 414C separately from measurement unit 415 for measuring the moisture content of the skin so as to eliminate an influence of the ambient conditions, it is also possible to make measurements only with capacitance detector 414A. In this case, a reference capacitance of an ambient condition may be detected as an initial value, and a difference from a capacitance measured via the skin may be determined. If the ambient conditions have little influence on measurement, skin-condition measurement device 414 may not necessarily include reference capacitance detector 414C, oscillation circuit 414D, or phase comparator 414E.

Capacitive moisture sensor that is skin-condition measurement device 414 is not limited to the circuit shown in FIG. 23, and may have various configurations. For example, instead of detecting capacitance with oscillation circuit 414B shown in FIG. 23, the capacitance may be detected based on the difference in amplitude. In this case, a lock-in amplifier may be used instead of oscillation circuit 414B, for example. While the signal representing the difference in the frequencies is converted to an analog voltage with F-V converter 414G according to Embodiment 8, the signal may be converted to a bus signal instead, using, for example, a frequency counter.

If portable terminal 401 has a bilateral communication function, information regarding skin conditions, such as moisture content or sebum content, of the skin may be sent to a server via a network, and cosmetic information suited to user's skin condition may be received from the server.

Figure 25:
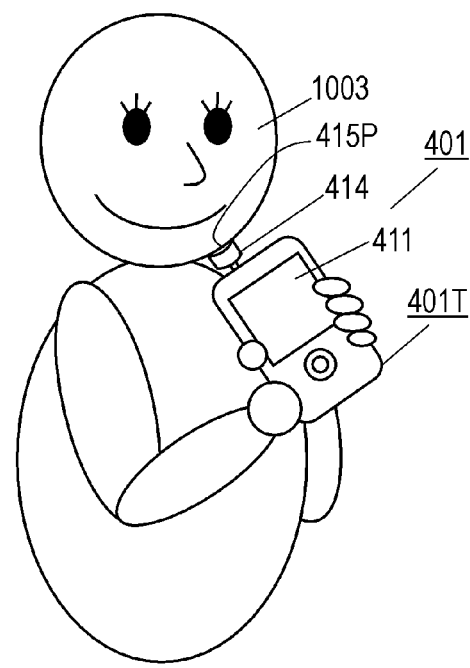
FIG. 25 is a schematic view of the portable terminal according to Embodiment 8 in use.
Figure 26:
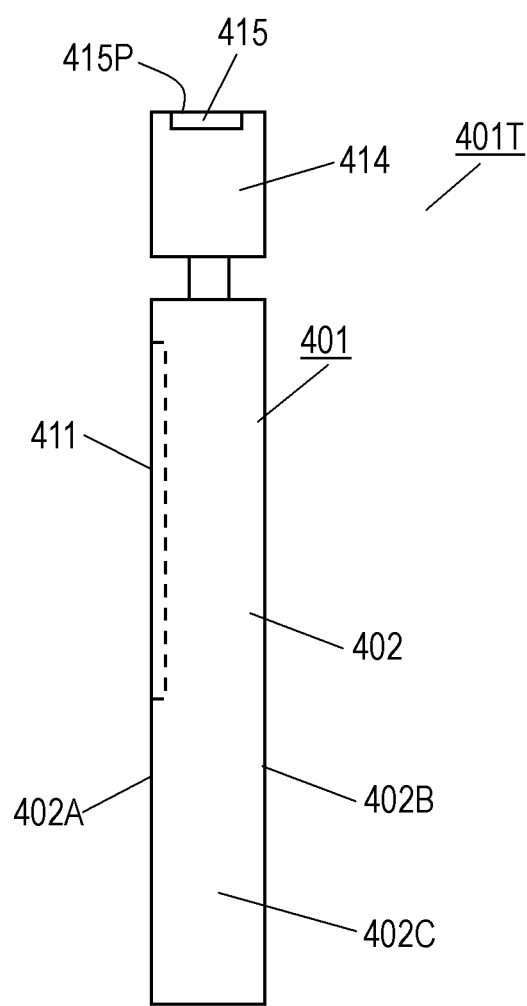
FIG. 26 is a side view of the portable terminal according to Embodiment 8.

FIG. 25 is a schematic view of portable terminal 401 according to Embodiment 8 when user 1003 measures a skin condition with skin-condition measurement device 414. FIG. 26 is a side view of portable terminal 401. User 1003 measures a skin condition by pressing measurement unit 415 of skin-condition measurement device 414 against, or bringing it close to, mainly his/her chin or cheek or under an upper arm.

According to Embodiment 8, as shown in FIG. 18, skin-condition measurement device 414 is attached to portable terminal 401 via earphone jack 404.

User 1003 may use a protection case that covers case 402 to protect portable terminal 401 from impact, or from design preferences. The protection case often covers the portable terminal almost entirely except for display screen 411, and usually has an opening therein to expose earphone jack 404. Therefore, according to Embodiment 8, skin-condition measurement device 414 can be mounted without removing the protection case to quickly measure the skin condition.

Since portable terminal 401 has earphone jack 404 that is configured to receive an earphone connected thereto, portable terminal 401 does not require another connection terminal or another opening in the protection case for connecting skin-condition measurement device 414, so that the portable terminal is highly versatile.

Skin-condition measurement device 414 per se does not require a power supply since using the power source of portable terminal 401, which reduces the size and weight.

User 1003 can remove skin-condition measurement device 414 from portable terminal (portable terminal body) 401. The recent trend is to decorate portable terminal 401 by inserting a decorative item of users' likings in earphone jack 404. Therefore, skin-condition measurement device 414 per se can have some design features to serve also as the decorative item.

Since skin-condition measurement device 414 is attached to portable terminal (portable terminal body) 401 according to Embodiment 8, as shown in FIG. 18, portable terminal 401T can have measurement unit 415 separated from display screen 411. In other words, as shown in FIG. 25, when user 1003 presses measurement unit 415 against or brings it close to the skin, display screen 411 can be kept away from the skin. Thus, display screen 411 is prevented from being contaminated with skin sebum or cosmetics.

As described above, according to Embodiment 8, user 1003 can readily attach skin-condition measurement device 414 to portable terminal (portable terminal body) 401 via earphone jack 404. Portable terminal 401 can be used substantially without changing its configurations. Since display screen 411 is kept away from measurement unit 415, portable terminal provides an advantage of contamination proof display screen 411.

Exemplary Embodiment 9

FIGS. 27A and 27B are side views of portable terminal 401A according to Exemplary Embodiment 9 of the present invention. In FIGS. 27A and 27B, components identical to those of portable terminal 401T or portable terminal (portable terminal body) 401 according to Embodiment 8 shown in FIGS. 18 to 26 are denoted by the same reference numerals. Portable terminal 401A according to Embodiment 9 includes skin-condition measurement device 514 instead of skin-condition measurement device 414 of portable terminal 401T according to Embodiment 8. Similarly to skin-condition measurement device 414 according to Embodiment 8, skin-condition measurement device 514 is attached to side-circumferential surface 402C of case 402 of portable terminal 401. Measurement unit 415 of skin-condition measurement device 414 according to Embodiment 8 shown in FIGS. 25 and 26 has measurement surface 415P that faces the skin of user 1003 when user 1003 measures the skin condition. Measurement surface 415P faces perpendicularly to a direction in which display screen 411 faces according to Embodiment 8 shown in FIGS. 25 and 26. Measurement surface 415P of measurement unit 415 of skin-condition measurement device 514 according to Embodiment 9 faces in a direction which inclines with respect to display screen 411 and which is away from display screen 411 of portable terminal 401.

If measurement surface 415P of measurement unit 415 of each of skin-condition measurement devices 414 and 514 is directed downward toward display screen 411, display screen 411 may contact the skin when measurement unit 415 is pressed against the skin.

However, in portable terminal 401T according to Embodiment 8 shown in FIG. 26, measurement unit 415 of skin-condition measurement device 414 faces in a direction away from display screen 411 and perpendicular to a direction in which display screen 411 faces. Thus, the skin of the user hardly contact display screen 411, and display screen 411 is prevented from being contaminated with skin sebum or cosmetics. Measurement surface 415P of measurement unit 415 of portable terminal 401A according to Embodiment 9 shown in FIG. 27A faces in a direction inclining with respect to display screen 411 and away from display screen 411. In other words, when plug 416 of skin-condition measurement device 414 or 514 is connected to earphone jack 404, measurement surface 415P of measurement unit 415 of skin-condition measurement device 414 or 514 faces in a direction which is away from display screen 411 and which is different from the direction in which display screen 411 faces. Thus, display screen 411 is prevented from contacting the skin, similarly to portable terminal 401T according to Embodiment 8.

Measurement surface 415P of skin-condition measurement device 414 or 514 faces in a direction which is away from display screen 411 and which inclines with respect to display screen 411, or in a direction perpendicular to and away from display screen 411. The user can press portable terminal 401 to the skin in the longitudinal direction of portable terminal 401 effortlessly by the principle of leverage.

Skin-condition measurement device 514 may be rotatable in rotating direction R401 about plug 416. In this case, as shown in FIG. 28B, measurement surface 415P may face toward rear surface 402B of portable terminal 401 when skin-condition measurement device 514 is in use so as to prevent display screen 411 from touching the skin.

Skin-condition measurement device 414 or 514 may be rotatable, or movable, about various axes, with respect to case 402 in various other manners to open in a direction different and away from the direction in which display screen 411 of portable terminal 401 faces.

Exemplary Embodiment 10

Figure 28:
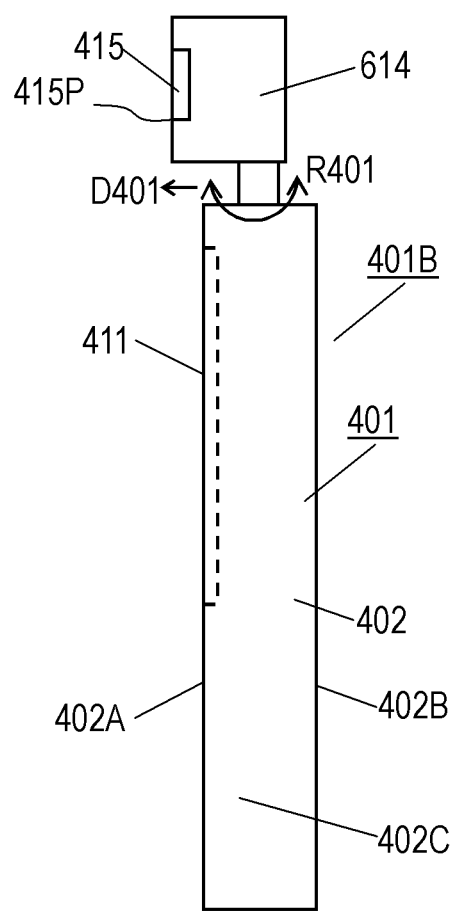
FIG. 28 is a side view of a portable terminal according to Exemplary Embodiment 10 of the present invention.

FIG. 28 is a side view of portable terminal 401B according to Exemplary Embodiment 10 of the present invention. In FIG. 28, components identical to those of portable terminal 401T or portable terminal (portable terminal body) 401 according to Embodiment 8 shown in FIGS. 18 to 26 are denoted by the same reference numerals. Portable terminal 401B according to Embodiment 10 includes skin-condition measurement device 614 instead of skin-condition measurement device 414 of portable terminal 401T according to Embodiment 8. Skin-condition measurement device 614 is attached to side-circumferential surface 402C of case 402 of portable terminal 401. Measurement surface 415P of measurement unit 415 of skin-condition measurement device 614 is substantially parallel to display screen 411 of portable terminal 401, and faces in a direction in which display screen 411 faces. As shown in FIG. 28, portable terminal 401B according to Embodiment 10 includes measurement unit 415 with measurement surface 415P protruding from display screen 411 in direction D401 extending from rear surface 402B to front surface 402A. That is, measurement unit 415 protrudes from display screen 411 in direction D401.

Skin-condition measurement device 614 may be movable with respect to case 402. Specifically, skin-condition measurement device 614 may be rotated in rotating direction R401 about plug 416 so that measurement surface 415P can face in the direction in which display screen 411 faces, and protrudes from display screen 411 in direction D401.

According to Embodiment 10, measurement surface 415P faces in the direction in which display screen 411 faces, and protrudes from display screen 411 in direction D401. Therefore, display screen 411 is prevented from contacting the skin, even though measurement unit 415 securely contacts, or is close to the skin.

In the case that portable terminal 401 has a phone call function, the user can press measurement surface 415P against the skin to measure the skin condition during a phone call. Since the microphone and speaker that are in fixed positions are kept near the mouth and ear during a phone call, respectively, skin-condition measurement device 614 can contact substantially the same particular position. This configuration increases repeatability of the measurement of the skin condition without the user being specifically aware of it.

Skin-condition measurement device 614 may be rotatable about various axes, or movable with respect to case 402 to face in the direction in which display screen 411 of portable terminal 401 faces to protrude from display screen 411 in direction D401.

While skin-condition measurement device 414, 514, or 614 is integral with plug 416 according to Embodiments 8 to 10, measurement unit 415 and plug 416 may be separate from each other and connected via a cable attached to the base of plug 416.

In the case that portable terminal (portable terminal body) 401 according to Embodiments 8 to 10 are a high-functional portable phone, portable terminal (portable terminal body) 401 may be a personal handy-phone system (PHS), a personal digital assistant (PDA), a personal computer, a portable tool, an electronic dictionary, an electronic calculator, or a game device, instead of the portable phone.

Terms, such as "front surface", "rear surface", "side-circumferential surface", and "side surface", indicating directions indicate relative directions depend only on relative positional relationships of constituent elements, such as a case or an earphone jack, of a portable terminal, and do not indicate absolute directions, such as a vertical direction.

INDUSTRIAL APPLICABILITY

A portable terminal according to the present invention can be carried and measure a skin condition easily with effortless operation, and is useful as a portable terminal with a function measuring a skin condition.

REFERENCE MARKS IN THE DRAWINGS 2 case
2A front surface 2B rear surface
3 display unit
4 skin-condition measurement sensor
6 display screen
9 measurement unit
10 camera module
11 imaging lens
12 battery
15 auxiliary cover
101 portable terminal
102 case
102A housing (first housing)
102B housing (second housing)
107 side-circumferential surface
112 corner
114 hinge
201 portable terminal
202 case
202A housing (first housing)
202B housing (second housing)
207 side-circumferential surface
212 corner
301 portable terminal
301B portable terminal
301C portable terminal
302 case
303 display unit
304 skin-condition measurement sensor
305 front surface
306 rear surface
307 side-circumferential surface
307A side surface (first side surface)
307B side surface (second side surface)
307C side surface (third side surface)
307D side surface (fourth side surface)
308 display screen
309 measurement unit
312 corner
313 battery
315 auxiliary cover
401 portable terminal (portable terminal body)
401T portable terminal
402 case
402A front surface
402B rear surface
402C side-circumferential surface
403 display unit
404 earphone jack
404A earphone
411 display screen
412 front plate
413A-413E contact
414 skin-condition measurement device
415 measurement unit
415P measurement surface
416 plug
417A-417C contact
418 skin-condition measurement circuit
419 audio circuit
420 plug
421A-421D contact
424 CPU
514 skin-condition measurement device
614 skin-condition measurement device

The invention claimed is:

1. A portable terminal configured to be utilized with an earphone connected to a first plug and with a skin-condition measurement device which includes a second plug, a measurement unit that measures a skin condition of a user, and a detection circuit connected to the measurement unit and the second plug, the portable terminal comprising:
   an earphone jack configured to receive the first plug of the earphone and the second plug of the skin-condition measurement device selectively inserted into the earphone jack;
   an audio circuit that supplies an electrical signal to the earphone via the earphone jack while the first plug of the earphone is inserted into the earphone jack;
   a skin-condition measurement circuit having an electrical signal input thereto from the second plug of the skin-condition measurement device via the earphone jack while the second plug of the skin-condition measurement device is inserted into the earphone jack; and
   a circuit switch unit that selects and switches one of the audio circuit and the skin-condition measurement circuit based on an electrical signal input to or output from the earphone jack.

2. The portable terminal according to claim 1, wherein the earphone jack includes a plurality of contacts functioning as a voltage supply, a ground point, and a data line, respectively.

3. The portable terminal according to claim 1, further comprising:
   a case having a plate shape having a front surface, a rear surface opposite to the front surface, and a side-circumferential surface connected to the front surface and the rear surface to surround the front surface and the rear surface, the case accommodating therein the earphone jack, the audio circuit, the skin-condition measurement circuit, and the circuit switch unit; and
   a display screen exposed from the front surface of the case, wherein the earphone jack is provided on the side-circumferential surface of the case,
   wherein the measurement unit of the skin-condition measurement device has a measurement surface that faces the user upon measuring a skin condition of the user, and
   wherein, when the second plug of the skin-condition measurement device is inserted into the earphone jack, the measurement surface of the measurement unit of the skin-condition measurement device faces in a direction that is different from a direction in which the display screen faces and that is away from the display screen.

4. The portable terminal according to claim 3, wherein, when the second plug of the skin-condition measurement device is inserted into the earphone jack, the measurement surface of the measurement unit of the skin-condition measurement device is movable with respect to the case.

5. The portable terminal according to claim 1, further comprising:
   a case having a plate shape having a front surface, a rear surface opposite to the front surface, and a side-circumferential surface connected to the front surface and the rear surface to surround the front surface and the rear surface, the case accommodating therein the earphone jack, the audio circuit, the skin-condition measurement circuit, and the circuit switch unit; and
   a display screen exposed from the front surface of the case, wherein the earphone jack is provided on the side-circumferential surface of the case,
   wherein the measurement unit of the skin-condition measurement device has a measurement surface that faces the user when measuring a skin condition Of the user, and
   wherein the measurement surface of the measurement unit of the skin-condition measurement device faces in a direction in which the display screen faces, and protrudes from the display screen in a direction from the rear surface toward the front surface.

6. The portable terminal according to claim 5, wherein, when the second plug of the skin-condition measurement device is inserted into the earphone jack, the measurement surface of the measurement unit of the skin-condition measurement device is movable with respect to the case.

7. The portable terminal according to claim 6, wherein, when the second plug of the skin-condition measurement device is inserted into the earphone jack, the measurement surface of the measurement unit of the skin-condition measurement device faces in a direction in which the rear surface faces, and can protrude from the rear surface in a direction from the front surface toward the rear surface.

8. A portable terminal configured to be utilized with an earphone connected to a first plug to measure a skin condition of a user, comprising:
   a skin-condition measurement device including
      a measurement unit that measures the skin condition of the user,
      a detection circuit connected to the measurement unit, and
      a second plug connected to the detection circuit; and
   a portable terminal body including
      an earphone jack configured to receive the first plug of the earphone and the second plug of the skin-condition measurement device selectively inserted into the earphone jack,
      an audio circuit that supplies electrical signals to the earphone via the earphone jack while the first plug of the earphone is inserted into the earphone jack,
      a skin-condition measurement circuit having an electrical signal input thereto from the second plug of the skin-condition measurement device via the earphone jack while the second plug of the skin-condition measurement device is inserted into the earphone jack, and
      a circuit switch unit that selects and switches one of the audio circuit and the skin-condition measurement circuit based on an electrical signal input to or output from the earphone jack.

9. The portable terminal according to claim 8, wherein the earphone jack includes a plurality of contacts functioning as a voltage supply, a ground point, and a data line, respectively.

10. The portable terminal according to claim 8,
   wherein the portable terminal body further includes:
      a case having a plate shape having a front surface, a rear surface opposite to the front surface, and a side-circumferential surface connected to the front surface and the rear surface to surround the front surface and the rear surface, the case accommodating therein the earphone jack, the audio circuit, the skin-condition measurement circuit, and the circuit switch unit; and
      a display screen exposed from the front surface of the case,
   wherein the earphone jack is provided on the side-circumferential surface of the case,
   wherein the measurement unit of the skin-condition measurement device has a measurement surface that faces the user upon measuring a skin condition of the user, and
   wherein, when the second plug of the skin-condition measurement device is inserted into the earphone jack, the measurement surface of the measurement unit of the skin-condition measurement device faces in a direction that is different in which the display screen faces and that is away from the display screen.

11. The portable terminal according to claim 10, wherein, when the second plug of the skin-condition measurement device is inserted into the earphone jack, the measurement surface of the measurement unit of the skin-condition measurement device is movable with respect to the case.

12. The portable terminal according to claim 8,
   wherein the portable terminal body further includes:
      a case having a plate shape having a front surface, a rear surface opposite to the front surface, and a side-circumferential surface connected to the front surface and the rear surface to surround the front surface and the rear surface, the case accommodating therein the earphone jack, the audio circuit, the skin-condition measurement circuit, and the circuit switch unit; and
      a display screen exposed from the front surface of the case,
   wherein the earphone jack is provided on the side-circumferential surface of the case,
   wherein the measurement unit of the skin-condition measurement device has a measurement surface that faces the user upon measuring a skin condition of the user, and
   wherein the measurement surface of the measurement unit of the skin-condition measurement device faces in a direction in which the display screen faces, and protrudes from the display screen in a direction from the rear surface toward the front surface.

13. The portable terminal according to claim 12, wherein, when the second plug of the skin-condition measurement device is inserted into the earphone jack, the measurement surface of the measurement unit of the skin-condition measurement device is movable with respect to the case.

14. The portable terminal according to claim 13, wherein, when the second plug of the skin-condition measurement device is inserted into the earphone jack, the measurement surface of the measurement unit of the skin-condition measurement device faces in a direction in which the rear surface faces, and can protrude from the rear surface in a direction from the front surface toward the rear surface.

* * * * *